(12) United States Patent
Scott et al.

(10) Patent No.: US 10,743,871 B2
(45) Date of Patent: Aug. 18, 2020

(54) SURGICAL CLIP APPLIER WITH DISTAL CLIP FEEDER

(71) Applicant: Ethicon, LLC, Guaynabo, PR (US)

(72) Inventors: Gregory Scott, Cincinnati, OH (US); Nathan Cummings, Blue Ash, OH (US); Tyler Brehm, Dayton, OH (US); Michael Stokes, Cincinnati, OH (US); Disha Labhasetwar, Cincinnati, OH (US); Joshua Young, Loveland, OH (US)

(73) Assignee: Ethicon, LLC, Guaynabo, PR (US)

( * ) Notice: Subject to any disclaimer, the term of this patent is extended or adjusted under 35 U.S.C. 154(b) by 136 days.

(21) Appl. No.: 15/885,952

(22) Filed: Feb. 1, 2018

(65) Prior Publication Data

US 2019/0231350 A1    Aug. 1, 2019

(51) Int. Cl.
*A61B 17/068*    (2006.01)
*A61B 17/08*    (2006.01)
(Continued)

(52) U.S. Cl.
CPC ........ *A61B 17/0682* (2013.01); *A61B 17/083* (2013.01); *A61B 17/105* (2013.01);
(Continued)

(58) Field of Classification Search
CPC . A61B 17/0682; A61B 17/083; A61B 17/105; A61B 17/128; A61B 17/1285;
(Continued)

(56) References Cited

U.S. PATENT DOCUMENTS 5,474,566 A * 12/1995 Alesi .................. A61B 17/1285
606/139
8,403,945 B2    3/2013 Whitfield et al.
(Continued)

FOREIGN PATENT DOCUMENTS

EP    0685204 A1    12/1995
EP    2412318 A2    2/2012

OTHER PUBLICATIONS

ISR/WO from PCT/IB2019/050345 (claiming priority to the present application) dated Mar. 29, 2019.

*Primary Examiner* — George J Ulsh
(74) *Attorney, Agent, or Firm* — Vorys, Sater, Seymour and Pease LLP

(57) ABSTRACT

End effectors with increased clip loading capacity include a housing having a tapered section at a distal end; first and second jaw members protruding distally from the tapered section; a surgical clip feeder arranged within the housing and configured to contain a plurality of surgical clips therein; and a feedbar longitudinally movable between the housing and the plurality of surgical clips, the feedbar having a distal portion engageable with a distal-most surgical clip of the plurality of surgical clips within the tapered section. The plurality of surgical clips is arrangeable within the surgical clip feeder at a non-zero angle with respect to a longitudinal axis of the end effector. Actuation of the feedbar engages and advances the distal-most surgical clip out of the surgical clip feeder and into interposition between the first and second jaw members.

20 Claims, 15 Drawing Sheets

(51) Int. Cl.
    *A61B 34/30*     (2016.01)
    *A61B 17/10*     (2006.01)
    *A61B 17/128*     (2006.01)
    *A61B 17/29*     (2006.01)
    *A61B 17/00*     (2006.01)

(52) U.S. Cl.
    CPC ........ *A61B 17/128* (2013.01); *A61B 17/1285* (2013.01); *A61B 34/30* (2016.02); *A61B 2017/003* (2013.01); *A61B 2017/00314* (2013.01); *A61B 2017/00327* (2013.01); *A61B 2017/2908* (2013.01); *A61B 2034/305* (2016.02)

(58) Field of Classification Search
    CPC .......... A61B 34/30; A61B 2017/00314; A61B 2017/00327; A61B 2017/2908; A61B 2034/305
    See application file for complete search history.

(56) References Cited

U.S. PATENT DOCUMENTS

| | | |
|---|---|---|
| 9,232,979 B2 | 1/2016 | Parihar et al. |
| 2011/0224696 A1 | 9/2011 | Huitema et al. |
| 2015/0127022 A1* | 5/2015 | Whitfield ........... A61B 17/1285 606/143 |
| 2016/0287252 A1 | 10/2016 | Parihar |

* cited by examiner

SURGICAL CLIP APPLIER WITH DISTAL CLIP FEEDER

BACKGROUND

Minimally invasive surgical (MIS) tools and procedures are often preferred over traditional open surgical approaches due to their propensity toward reducing post-operative recovery time and leaving minimal scarring. Endoscopic surgery is one type of MIS procedure in which a surgical tool operably connected to an elongate shaft is introduced into the body of a patient through a natural bodily orifice. Laparoscopic surgery is a related type of MIS procedure in which one or more small incisions are formed in the abdomen of a patient and a trocar is inserted through each incision to form a surgical access pathway for a surgical tool and elongate shaft. Once located within the abdomen, the surgical tool may engage and/or treat tissue in a number of ways to achieve a diagnostic or therapeutic effect. Manipulation and engagement of the surgical tool may take place via various components passing through the elongate shaft.

Robotic surgery represents a specialized class of laparoscopic surgical procedures. Instead of directly engaging a surgical tool, as in traditional laparoscopic surgery, a surgeon in a robotic surgical procedure manipulates and engages the surgical tool using an electronic interface communicatively coupled to a robotic manipulator. Manipulation and engagement of a surgical tool under robotic control can allow much more precise surgical procedures to be performed in many instances. To provide natural, hand-like articulation during a robotic surgical procedure, robotic surgical tools may incorporate an articulable "wrist" that couples an end effector to the elongate shaft. As used herein, the term "end effector" refers to the clinically active portion of a surgical tool. The wrist can also facilitate an expanded and more complex range of motion than is possible with a human wrist, which can allow highly elaborate and precise surgical procedures to be performed.

The end effectors of MIS tools are often similar in design to tools used in traditional surgical procedures, with the exception of the MIS tools being sized to extend through a trocar and configured for actuation using one or more components extending through the elongate shaft. One type of MIS tool comprises a clip applier as an end effector, which can be used to ligate blood vessels, ducts, shunts, or portions of a bodily tissue during a surgical procedure. Clip appliers used in MIS procedures include a pair of movable opposed jaw members at a distal end of the surgical tool for manipulating and crimping a surgical clip ("ligation clip") in between. In operation, a physician may position the opposed jaw members and an open surgical clip around a vessel, duct, or similar structure and actuate the surgical tool to bring the jaw members together, thereby collapsing the surgical clip to shut off fluid flow through the vessel or duct.

During the course of a MIS procedure, a surgeon may need to place multiple surgical clips in succession on one or more anatomical structures. Although MIS clip appliers may include a single surgical clip, it can be more desirable for multiple surgical clips to be housed in the clip applier to allow completion of a MIS procedure with a single insertion of the clip applier to a surgical site. Otherwise, a surgeon may have to utilize multiple clip appliers or withdraw the clip applier from a surgical site, load a new surgical clip into the end effector, and then reintroduce the clip applier to the surgical site. Both of these approaches may increase the time, complexity, cost and risk of a MIS procedure. Accordingly, clip appliers capable of housing multiple surgical clips can be desirable.

Wristed clip appliers presently available for MIS procedures have several significant limitations. The wrist architecture in conventional MIS tools generally precludes feeding finished surgical clips through the wrist to reach the opposed jaw members of the end effector. As a result, wristed clip appliers may incorporate one or more surgical clips distal to the wrist for feeding into the opposed jaw members. Because the space distal to the wrist is small, however, the number of surgical clips that may be housed in this location is rather limited. In some instances, the number of surgical clips housed distal to the wrist may be insufficient to complete a given surgical procedure. Conventional loading approaches may be similar to those described in U.S. Pat. No. 5,743,456, which is incorporated herein by reference in its entirety.

Moreover, increasing the size of the surgical tool distal to the wrist so that more surgical clips may be accommodated can be problematic in its own right. Specifically, a larger distal tool size increases the tool length undergoing articulation (i.e., a longer end effector), which can make accurate articulation more difficult. In addition, a larger tool size distal to the wrist may render the surgical tool incompatible with other components used in a surgical procedure.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is directed to end effectors for surgical clip appliers and related surgical tools and, more particularly, to surgical clip appliers having improved clip loading capacity, particularly wristed surgical clip appliers.

As discussed above, supplying surgical clips to a wristed clip applier can be problematic, due both to the difficulty of feeding surgical clips through the wrist and housing a sufficient number of surgical clips within the surgical tool for eventual deployment during a surgical procedure. These issues are often not mutually exclusive of one another, since housing surgical clips distal to the wrist to address the feeding issue places the surgical clips in a location where a limited number of surgical clips may be housed. The present disclosure describes various approaches for promoting more efficient packing and dispensation of surgical clips distal to the wrist in a wristed clip applier without significantly increasing the size (length) of the distal portion of the surgical tool, specifically the end effector. In addition, to the advantage of increasing the number of surgical clips stored distal to the wrist, certain tool configurations of the present disclosure also beneficially allow surgical clips of varying size and/or type to be deployed from a single surgical clip applier, thereby increasing the breadth of surgical procedures that may be performed. The various tool configurations disclosed herein may afford other benefits as well, as will become apparent to one having ordinary skill in the art upon reading the present disclosure. Moreover, it is to be further appreciated that the clip packing and dispensation features of the present disclosure may likewise be incorporated in non-wristed surgical clip appliers and similar surgical tools while still affording at least some of the advantages described herein.

Before discussing additional details of the surgical clip appliers of the present disclosure and methods for their use, a brief overview of laparoscopic and similar surgical tools and robotic surgical systems will be provided hereinafter in order for the embodiments of the present disclosure to be better understood.

Figure 1:
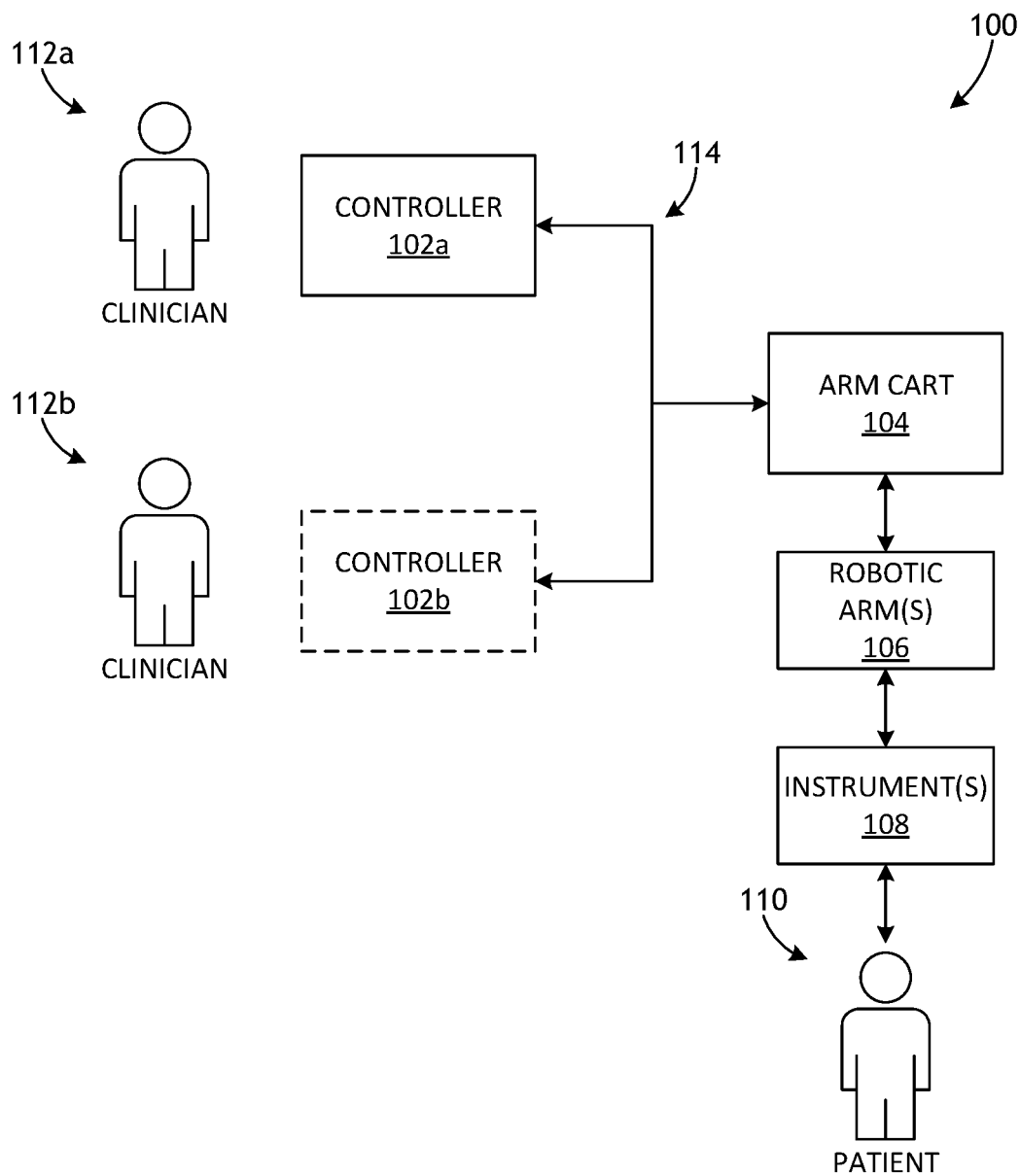
FIG. 1 is a block diagram of an example robotic surgical system that may incorporate some or all of the principles of the present disclosure.

FIG. 1 is a block diagram of an illustrative robotic surgical system that may incorporate some or all of the principles of the present disclosure. As illustrated, robotic surgical system 100 can include at least one master controller 102a and at least one arm cart 104. Arm cart 104 may be mechanically and/or electrically coupled to a robotic manipulator and, more particularly, to one or more robotic arms 106 or "tool drivers." Each robotic arm 106 may include and otherwise provide a location for mounting one or more surgical tools or instruments 108 for performing various surgical tasks on patient 110. Operation of robotic arm(s) 106 and instrument (s) 108 may be directed by clinician 112a (e.g., a surgeon) from master controller 102a.

In some embodiments, second master controller 102b (shown in dashed lines) operated by second clinician 112b may also direct operation of robotic arm(s) 106 and instrument(s) 108 in conjunction with first clinician 112a. For example, clinicians 112a and 112b may control different robotic arms 106 or, in some cases, complete control of robotic arms 106 may be passed between clinicians 112a and 112b. In some embodiments, additional arm carts (not shown) having additional robotic arms (not shown) may be utilized during a surgical procedure on patient 110, and these additional robotic arms may be controlled by one or more of master controllers 102a and 102b.

Arm cart 104 and master controllers 102a and 102b may be in communication with one another via communications link 114, which may be any type of wired or wireless telecommunication means configured to carry a variety of communication signals (e.g., electrical, optical, infrared, and the like) according to any communication protocol.

Master controllers 102a and 102b may include one or more physical controllers (not shown) that can be grasped by clinicians 112a and 112b and manipulated in space while viewing a procedure via a stereo display. The physical controllers may comprise manual input devices movable in multiple degrees of freedom, optionally including an actuatable handle for actuating instrument(s) 108. For example, actuation of instrument(s) 108 may include one or more of opening and closing opposing jaws, applying an electrical potential (current) to an electrode, or the like. Master controllers 102a and 102b can also include an optional feedback meter viewable by clinicians 112a and 112b via a display to provide a visual indication of various metrics of instrument(s) 108, such as the amount of force being applied to the surgical tool (e.g., via a cutting instrument or dynamic clamping member).

Example implementations of robotic surgical systems, such as robotic surgical system 100, are disclosed in U.S. Pat. No. 7,524,320, the contents of which are incorporated herein by reference in their entirety. Various aspects of such robotic surgical systems are not described in further detail herein beyond that needed to understand one or more of the various embodiments of robotic surgical apparatuses, systems, and methods disclosed herein.

Figure 2:
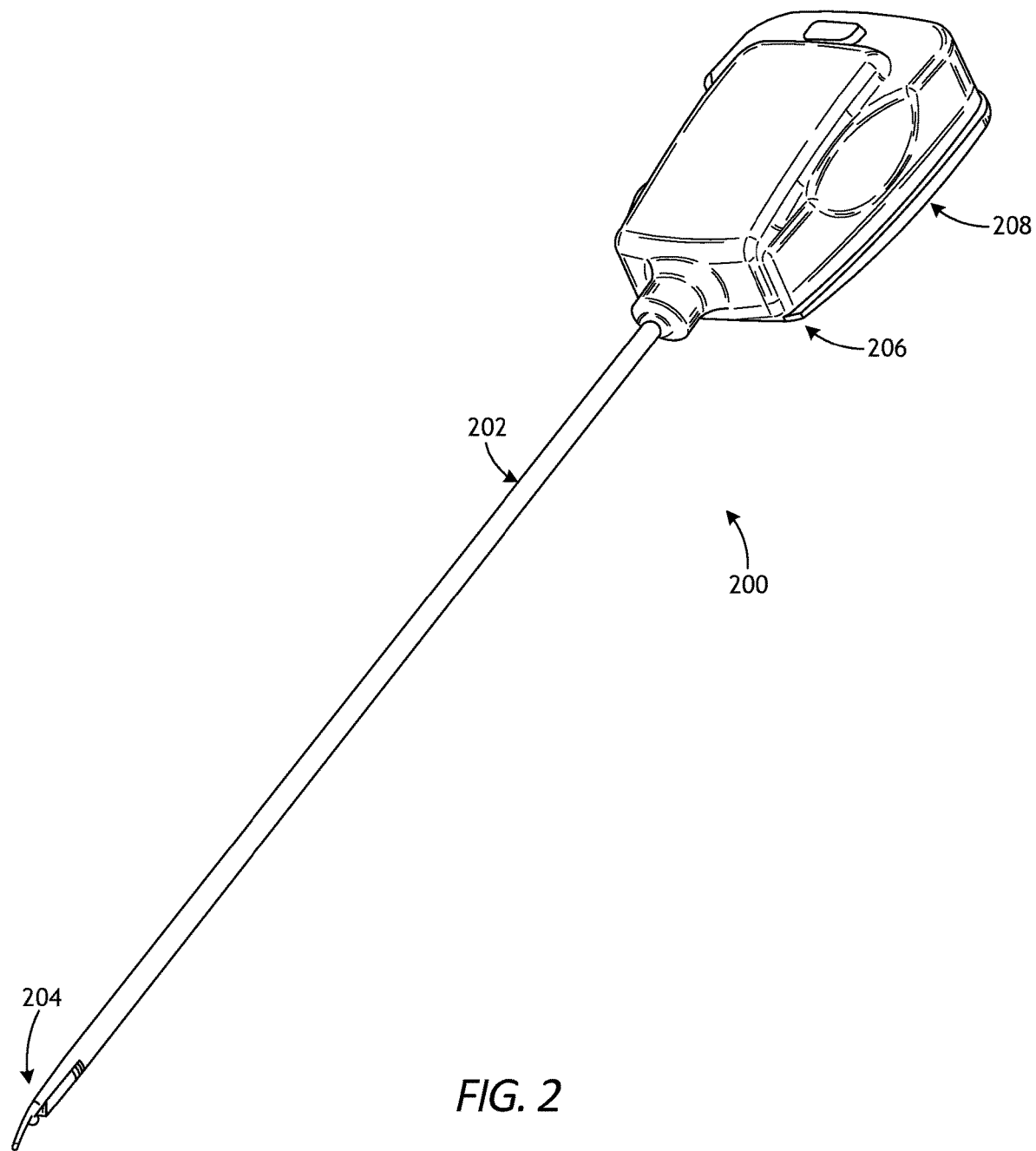
FIG. 2 is an isometric top view of an illustrative surgical tool that may incorporate some or all of the principles of the present disclosure.

FIG. 2 is an isometric top view of illustrative surgical tool 200 that may incorporate some or all of the principles of the present disclosure. Surgical tool 200 may be the same as or similar to instrument(s) 108 of FIG. 1 and, therefore, may be used in conjunction with robotic surgical system 100 of FIG. 1. Accordingly, surgical tool 200 may be designed for releasable coupling to robotic arm 106 (FIG. 1) of a robotic manipulator within robotic surgical system 100 or a similar robotic surgical system. Surgical tool 200 may be a surgical clip applier, according to some embodiments, as described in further detail in the present disclosure. Additional disclosure concerning surgical clip appliers is provided in U.S. Patent Application Publications 2016/0287252 and 2011/0224696, the contents of which are hereby incorporated by reference in their entirety.

While surgical tool 200 is described herein with reference to a robotic surgical system, it is to be appreciated that the principles of the present disclosure are similarly applicable to non-robotic MIS tools or, more specifically, manually operated MIS tools. Similarly, the principles of the present disclosure are also applicable to conventional laparoscopic and endoscopic surgical tools, according to some embodiments, both those incorporating a wrist and those that do not. Accordingly, the discussion provided herein relating to robotic surgical systems merely encompasses one example application of the presently disclosed embodiments.

As illustrated, surgical tool 200 includes elongate shaft 202, end effector 204 coupled to the distal end of elongate shaft 202, and drive housing 206 coupled to the proximal end of elongate shaft 202. The terms "proximal" and "distal" are defined herein relative to a robotic surgical system having an interface configured to mechanically and/or electrically couple surgical tool 200 (e.g., via drive housing 206) to a robotic manipulator. The term "proximal" refers to positioning of an element closer to the robotic manipulator or drive housing 206, and the term "distal" refers to positioning of an element closer to end effector 204 and thus further away from the robotic manipulator or drive housing 206. For non-robotically controlled MIS tools, the terms "proximal" and "distal" are defined similarly with respect to the location of engagement of the surgical tool by a surgeon. Moreover, use of directional terms such as above, below, upper, lower, upward, downward, left, right, and the like are used in the description herein in relation to the illustrative embodiments as they are depicted in the figures, the upward or upper direction being toward the top of the corresponding figure and the downward or lower direction being toward the bottom of the corresponding figure.

In applications where surgical tool 200 is used in conjunction with a robotic surgical system (e.g., system 100 of FIG. 1), drive housing 206 may include tool mounting portion 208 designed with features adapted to releasably couple surgical tool 200 to a robotic arm (e.g., robotic arm(s) 106 or "tool drivers" of FIG. 1) of a robotic manipulator. Tool mounting portion 208 may releasably attach (couple) drive housing 206 to a robotic arm in a variety of ways, such as clamping, clipping, slidable mating, or magnetic engagement. In some embodiments, tool mounting portion 208 may include an array of electrical connecting pins, which may be coupled to an electrical connection on the mounting surface of the robotic arm. While tool mounting portion 208 is described herein with reference to mechanical, electrical, and magnetic coupling elements, it should be understood that a wide variety of telemetry modalities may also be used, including infrared, inductive coupling, or the like.

Figure 3:
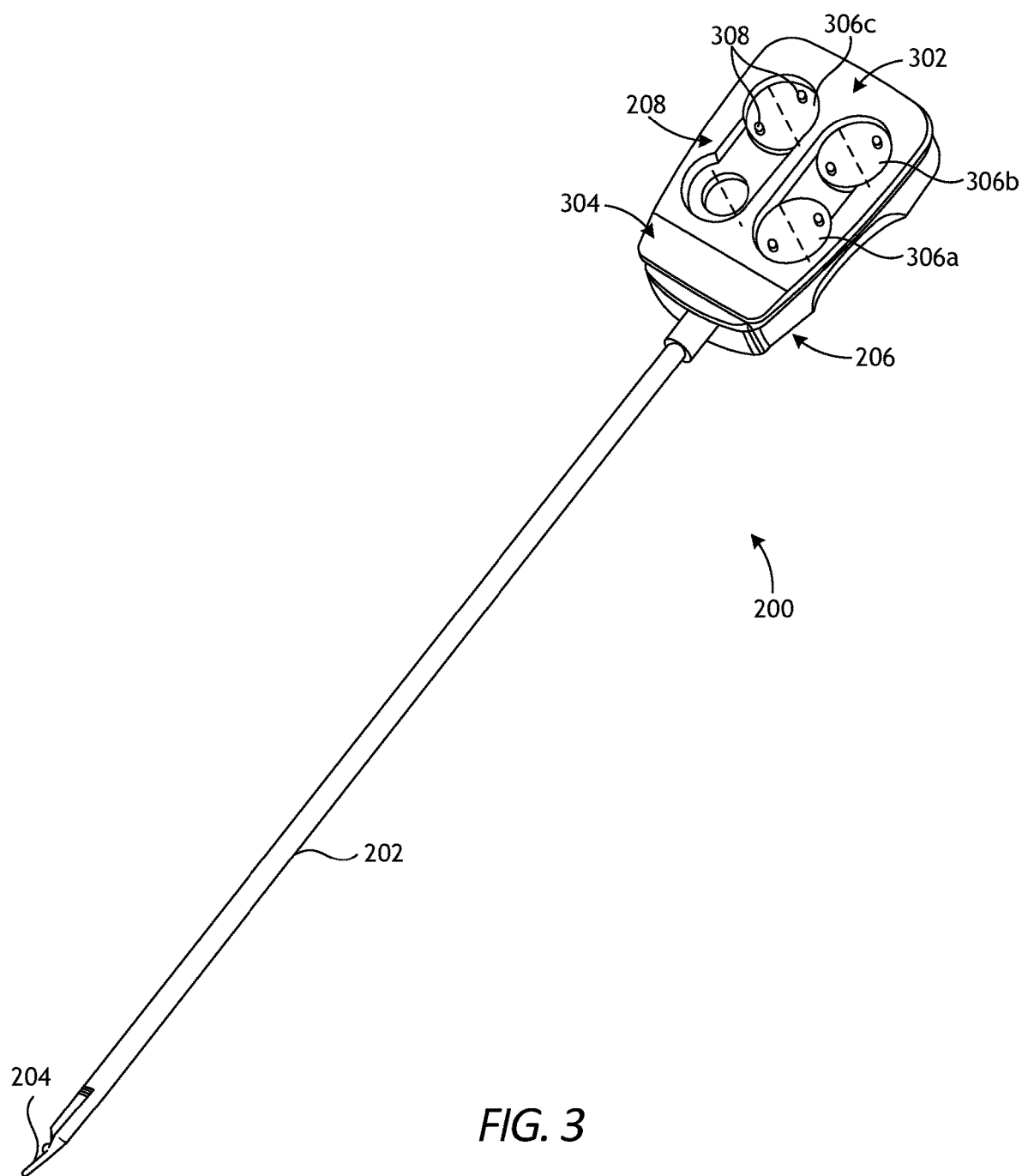
FIG. 3 is an isometric bottom view of the illustrative surgical tool of FIG. 2.

FIG. 3 is an isometric bottom view of illustrative surgical tool 200, which includes interface 302 that mechanically and/or electrically couples tool mounting portion 208 to a robotic manipulator. In various embodiments, tool mounting portion 208 includes tool mounting plate 304 that operably supports a plurality of drive inputs, shown as first drive input 306a, second drive input 306b, and third drive input 306c. While three drive inputs 306a-c are shown in FIG. 3, more or less than three may be employed, without departing from the scope of the present disclosure.

In the illustrated embodiment, each drive input 306a-c comprises a rotatable disc configured to align with and couple to a corresponding input actuator (not shown) of a corresponding robotic manipulator. Moreover, each drive input 306a-c provides or defines one or more surface features 308 configured to align with mating surface features provided on the corresponding input actuator. Surface features 308 can include, for example, various protrusions and/or indentations that are positioned to facilitate a mating engagement.

Figure 4:
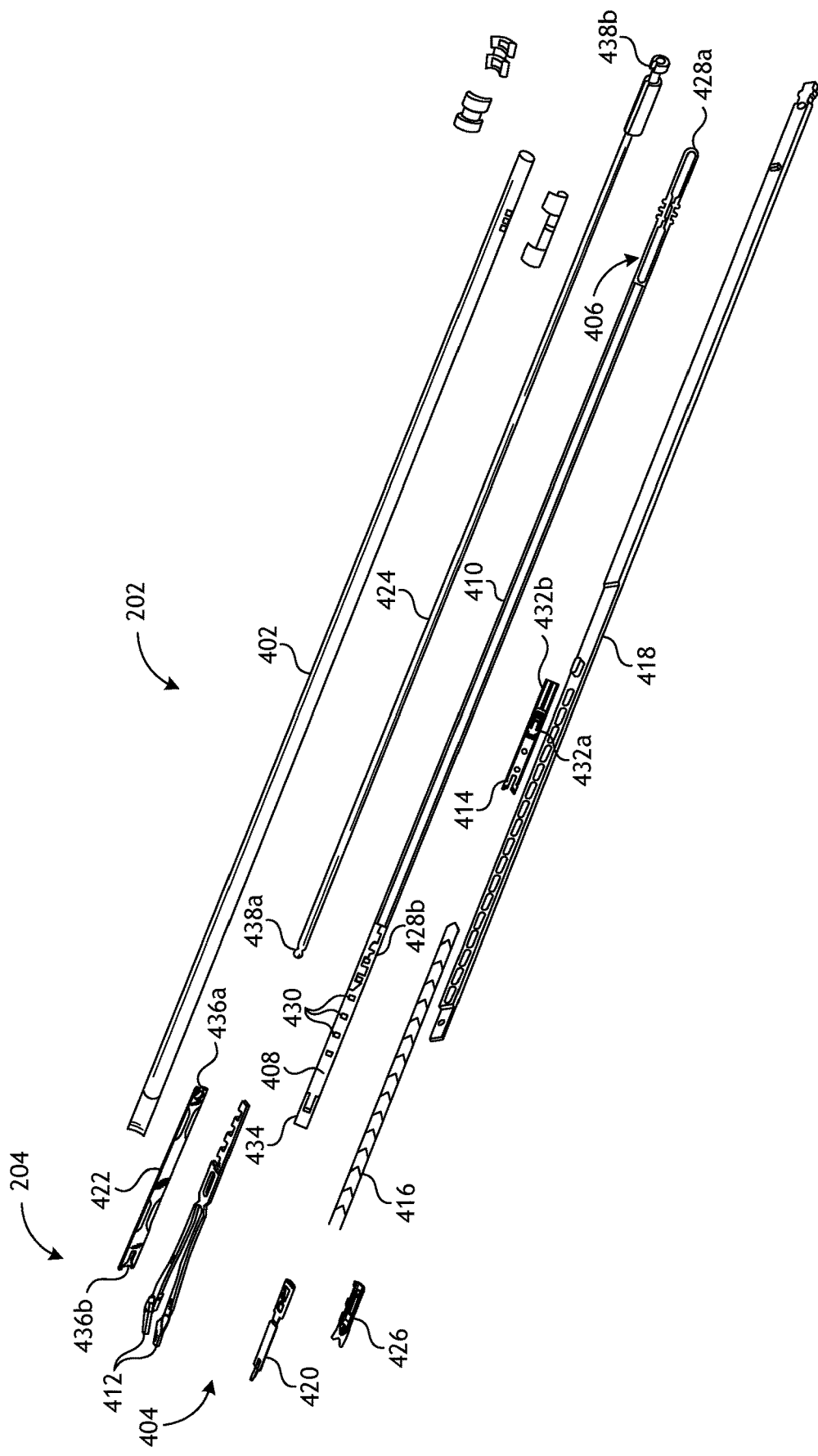
FIG. 4 is an exploded view of the elongate shaft and the end effector of the illustrative surgical tool of FIG. 2.

FIG. 4 is an exploded view of one example of elongate shaft 202 and end effector 204 within surgical tool 200, as depicted in FIGS. 2 and 3, according to one or more embodiments. In the illustrated embodiment, end effector 204 is configured as a surgical clip applier, the features and operational details of which are discussed hereinafter.

As illustrated in FIG. 4, elongate shaft 202 includes outer tube 402, which houses various components of elongate shaft 202 therein, including jaw retaining assembly 404. Jaw retaining assembly 404 includes jaw retainer shaft 406 with clip track 408 and push rod channel 410 formed thereon. End effector 204 also includes opposing jaw members 412 that are configured to mate to a distal end of clip track 408.

Elongate shaft 202 also includes a clip advancing assembly, which, in one example embodiment, can include feeder shoe 414 adapted to be slidably disposed within clip track 408. Feeder shoe 414 is designed to sequentially advance a series of surgical clips 416 positioned within clip track 408. Feedbar 418 is adapted to drive feeder shoe 414 through clip track 408 to affect advancement of surgical clips 416. Advancer component 420 is adapted to mate to a distal end of feedbar 418 for advancing a distal-most surgical clip into interposition between jaw members 412. Tissue stop 426 can mate to a distal end of clip track 408 to aid in positioning jaw members 412 relative to a surgical site.

Elongate shaft 202 furthers include a clip forming assembly operable to urge jaw members 412 toward one another and thereby crimp (crush) the distal-most surgical clip placed into interposition between jaw members 412 by the clip advancement assembly (surgical clip interposition not shown in FIG. 4). As depicted in FIG. 4, the clip forming assembly comprises a camming assembly. The camming assembly includes cam 422 that slidably mates to jaw members 412, and push rod 424 that moves cam 422 longitudinally relative to jaw members 412.

Longitudinal movement of cam 422 may urge jaw members 412 to collapse together to affect crimping. It is to be appreciated that other structures to urge jaw members 412 together may be utilized in alternative embodiments of the present disclosure.

Jaw retainer shaft 406 is extendable within and couples to outer tube 402 at proximal end 428a, with distal end 428b being adapted to mate with jaw members 412. Push rod channel 410 formed on jaw retainer shaft 406 may be configured to slidably receive push rod 424, which is used to advance cam 422 over jaw members 412. Clip track 408 extends distally beyond distal end 428b of jaw retainer shaft 406 to allow a distal end of clip track 408 to be substantially aligned with jaw members 412.

Clip track 408 can include one or more openings 430 formed therein for receiving upper or "superior" tang 432a formed on feeder shoe 414 and adapted to be disposed within clip track 408. Clip track 408 can also include stop tang 434 formed thereon that is effective to become engaged by a corresponding stop tang (not shown in FIG. 4) formed on feeder shoe 414 to prevent movement of feeder shoe 414 beyond a specified distal-most position. To facilitate proximal movement of feeder shoe 414 within clip track 408, feeder shoe 414 can also include lower or "inferior" tang 432b formed on the underside thereof for allowing feeder shoe 414 to become engaged by feedbar 418 as feedbar 418 is moved distally. In use, each time feedbar 418 is moved distally, a detent formed in feedbar 418 engages inferior tang 432b and moves feeder shoe 414 distally a predetermined distance within clip track 408. Feedbar 418 can then be moved proximally to return to or near its initial position. The angle of inferior tang 432b allows inferior tang 432b to slide into the next detent formed in feedbar 418.

Jaw members 412 are movable (collapsible) relative to one another and are configured to receive therebetween a distal-most surgical clip from surgical clips 416. Jaw members 412 may each include a groove formed on opposed inner surfaces thereof for receiving the legs of an interposed surgical clip in alignment with jaw members 412. In the illustrated embodiment, jaw members 412 are biased to an open position and a force is required to urge opposed jaw members 412 toward one another to crimp the interposed surgical clip (not shown in FIG. 4).

Jaw members 412 can also each include a cam track formed thereon for allowing cam 422 to slidably engage and move opposed jaw members 412 toward one another. Proximal end 436a of cam 422 is mateable with distal end 438a of push rod 424, and distal end 436b of cam 422 is adapted to engage and actuate jaw members 412. Proximal end 438b of push rod 424 is mateable with a closure link assembly associated with drive housing 206 for moving push rod 424 and cam 422 relative to jaw members 412.

Distal end 436b of cam 422 includes a camming channel or tapering recess formed therein for slidably receiving corresponding cam tracks provided by jaw members 412. In operation, cam 422 is advanced from a proximal position, in which jaw members 412 are spaced apart from one another, to a distal position, where jaw members 412 are collapsed to a closed position. As cam 422 is advanced over jaw members 412, the tapering recess at distal end 436b serves to urge jaw members 412 toward one another, thereby crimping an interposed surgical clip.

Figure 5:
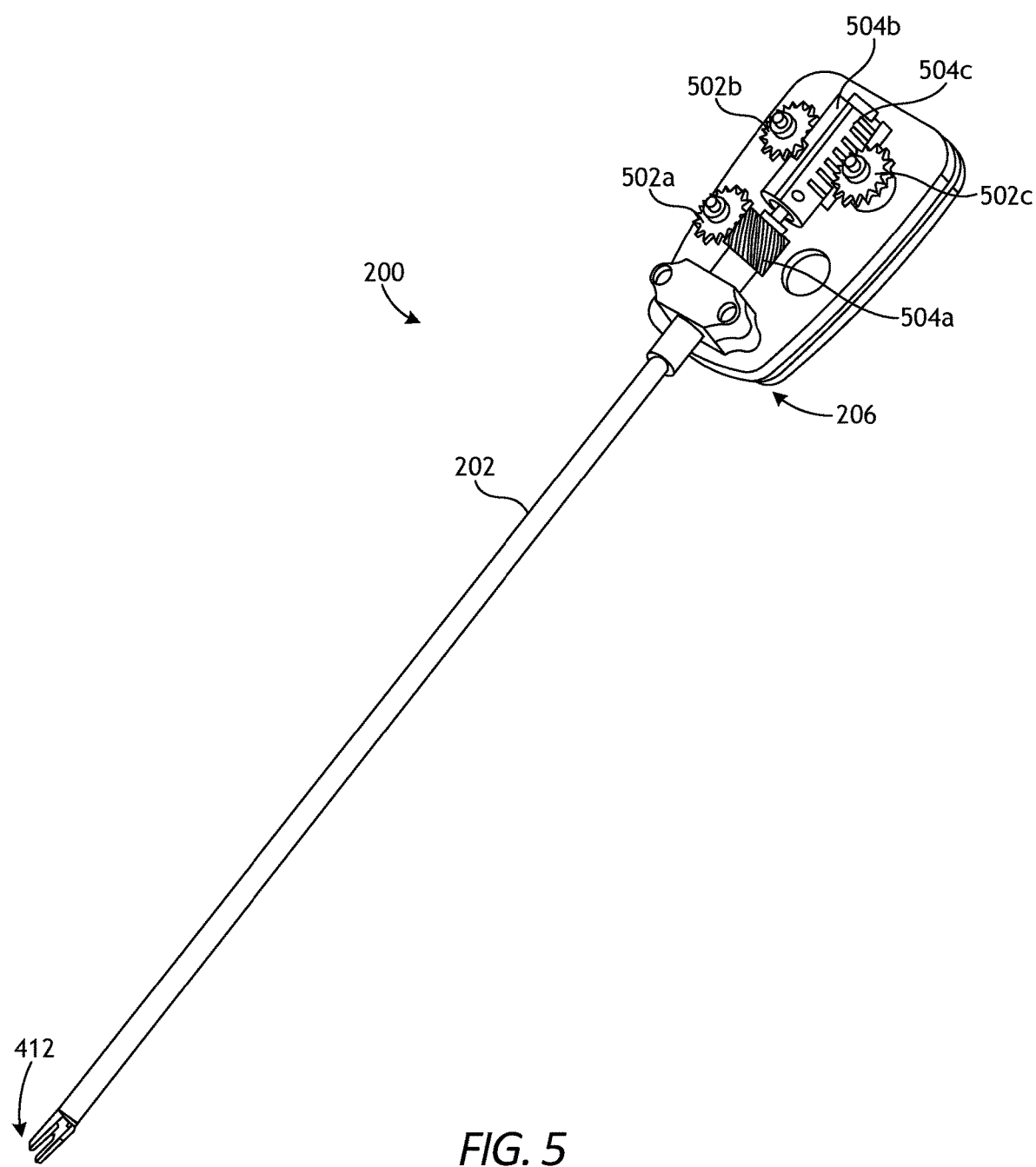
FIG. 5 is an exposed isometric view of the illustrative surgical tool of FIG. 2.

FIG. 5 is an exposed isometric view of illustrative surgical tool 200 of FIG. 2, according to one or more embodiments. In FIG. 5, the shroud or covering of drive housing 206 has been removed to reveal various internal component parts. As illustrated, surgical tool 200 may include first drive gear 502a, second drive gear 502b, and third drive gear 502c. First drive gear 502a may be operatively coupled to (or extend from) first drive input 306a (FIG. 3) such that actuation of first drive input 306a correspondingly rotates first drive gear 502a. Similarly, second and third drive gears 502b and 502c may be operatively coupled to (or extend from) corresponding second and third drive inputs 306b and 306c (FIG. 3), respectively, such that actuation of second and third drive inputs 306b and 306c correspondingly rotates second and third drive gears 502b and 502c, respectively.

First drive gear 502a may be configured to intermesh with first driven gear 504a, which is operatively coupled to elongate shaft 202. In the illustrated embodiment, first drive gear 502a and first driven gear 504a comprise mating helical gears. In operation, rotation of first drive gear 502a about a first axis correspondingly rotates first driven gear 504a about a second axis orthogonal to the first axis to control rotation of elongate shaft 202 in clockwise and counterclockwise directions based on the rotational direction of first drive gear 502a.

Second drive gear 502b may be configured to intermesh with second driven gear 504b (partially visible in FIG. 5), and third drive gear 502c may be configured to intermesh with third driven gear 504c. In the illustrated embodiment, second and third drive gears 502b and 502c and second and third driven gears 504b and 504c collectively comprise corresponding rack and pinion interfaces, where second and third driven gears 504b and 504c comprise the rack portion and second and third drive gears 502b and 502c comprise the pinion portion. Independent rotation of second and third drive gears 502b and 502c causes second and third driven gears 504b and 504c, respectively, to translate linearly relative to and independent of one another.

In at least one embodiment, actuation (rotation) of third drive gear 502c results in a distal-most surgical clip 416 (FIG. 4) being fed into interposition between jaws members 412. More particularly, third driven gear 504c may be operatively coupled to feedbar 418 (FIG. 4) and, upon rotation of third drive gear 502c in a first angular direction, third driven gear 504c may advance distally and correspondingly advance feedbar 418 a sufficient distance to advance surgical clip 416 into interposition between jaw members 412. Rotation of third drive gear 502c may be precisely controlled by an electrical and software interface to translate third driven gear 504c a sufficient distance to feed surgical clip 416 into jaw members 412.

Upon delivery of surgical clip 416 into interposition between jaw members 412, or after a predetermined amount of rotation of third drive gear 502c, rotation of third drive gear 502c may be reversed in a second angular direction to move third driven gear 504c linearly in a proximal direction, which correspondingly retracts feedbar 418 proximally. This process may be repeated as needed to deploy any remaining surgical clips 416 in a desired location.

Actuation of second drive gear 502b may urge jaw members 412 to close or collapse to affect crimping of an interposed surgical clip (not shown in FIG. 5). More particularly, second driven gear 504b may be coupled to proximal end 438b (FIG. 4) of push rod 424 (FIG. 4) and, upon actuation of second drive gear 502b in a first angular direction, second driven gear 504b may advance linearly in a distal direction and correspondingly drive push rod 424 distally. Distal advancement of push rod 424 may drive cam 422 over a portion of jaw members 412 to affect closure thereof and promote crimping of the interposed surgical clip. Once the interposed surgical clip has been successfully deployed and crimped, rotation of second drive gear 502b in the opposite angular direction may move second driven gear 504b proximally. This action correspondingly moves push rod 424 and cam 422 proximally and permits jaw members 412 to open once again.

The processes for delivering surgical clips 416 into jaw members 412 and collapsing jaw members 412 to affect crimping are not limited to the actuation mechanisms and structures described herein. In alternative embodiments, for example, second and third driven gears 504b and 504c may instead comprise capstan pulleys configured to route and translate drive cables within elongate shaft 202. In such embodiments, the drive cables may be operatively coupled to one or more lead screws or other types of rotating members positioned within elongate shaft 202 near the distal end thereof. The drive cables may be similarly capable of advancing feedbar 418 to deliver surgical clips 416 into jaw members 412 and advancing cam 422 to collapse jaw members 412 to promote crimping.

Figure 6:
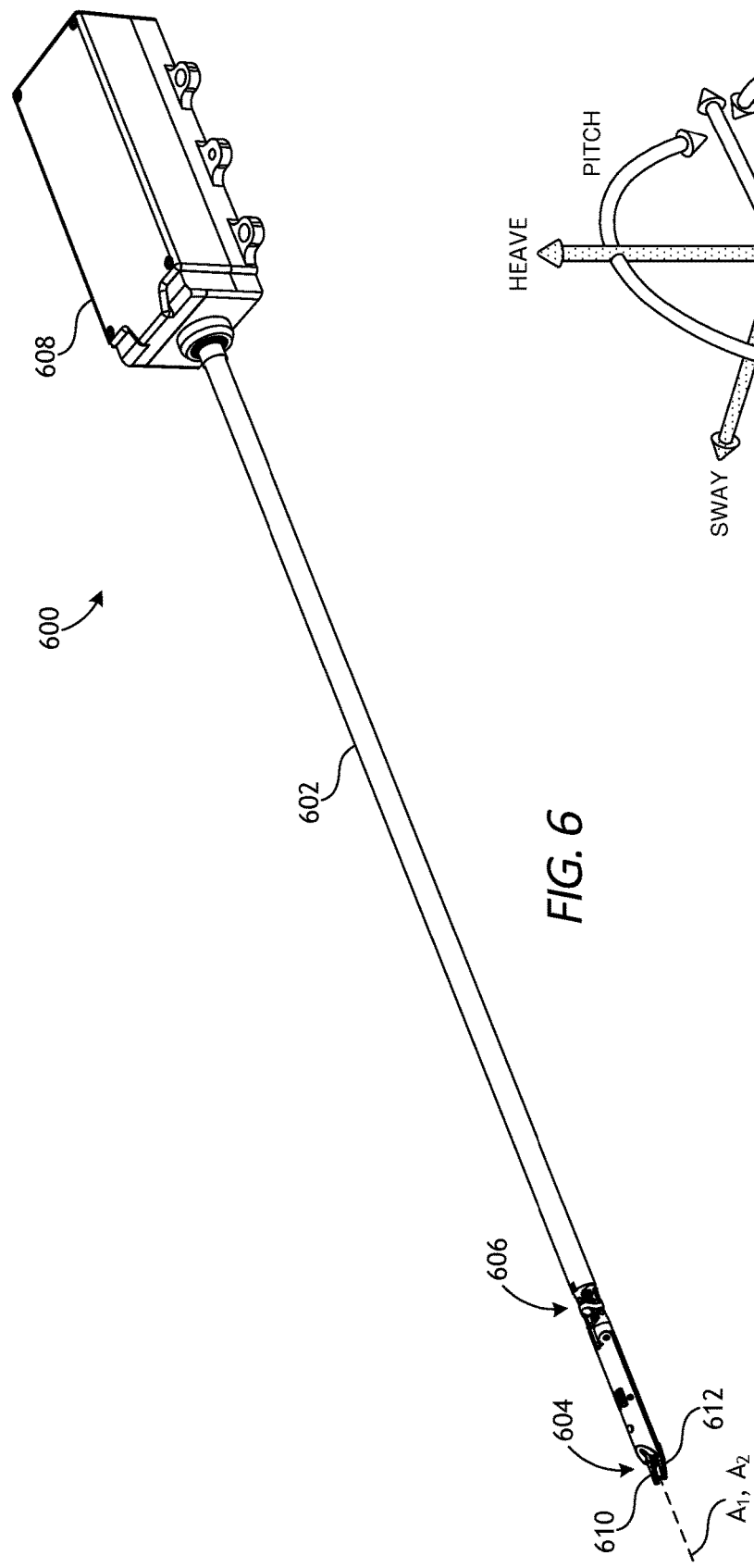
FIG. 6 is an isometric top view of another illustrative surgical tool that may incorporate some or all of the principles of the present disclosure.

FIG. 6 is an isometric top view of another illustrative surgical tool 600 that may incorporate some or all of the principles of the present disclosure. Similar to surgical tool 200 of FIG. 2, surgical tool 600 may be used in conjunction with robotic surgical system 100 of FIG. 1 or a similar robotic surgical system. As illustrated, surgical tool 600 includes elongate shaft 602, end effector 604 positioned at the distal end of elongate shaft 602, wrist 606 (alternately referred to as an "articulable wrist joint") that couples end effector 604 to the distal end of elongate shaft 602, and drive housing 608 coupled to the proximal end of elongate shaft 602. In some embodiments, elongate shaft 602, and hence end effector 604 coupled thereto, may be configured to rotate about longitudinal axis $A_1$.

As illustrated, end effector 604 comprises a surgical clip applier that includes opposing jaw members 610 and 612 configured to collapse toward one another to crimp a surgical clip in a manner similar to that described in detail above for surgical tool 200. Wrist 606 comprises an articulable joint that facilitates pivoting movement of end effector 604 relative to elongate shaft 602 to position end effector 604 at a desired orientation and location relative to a surgical site. Housing 608 includes (contains) various actuation mechanisms designed to control articulation and operation of end effector 604.

Figure 7:
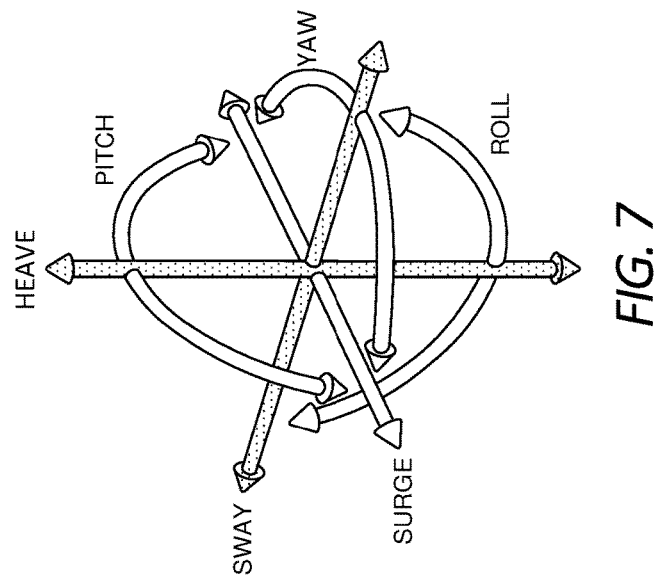
FIG. 7 illustrates the potential degrees of freedom through which a wrist of a surgical tool may be able to articulate (pivot).

FIG. 7 illustrates the potential degrees of freedom through which wrist 606 may be able to articulate (pivot). The degrees of freedom available to wrist 606 are represented by three translational variables (i.e., surge, heave, and sway), and by three rotational or orientation variables (i.e., Euler angles or roll, pitch, and yaw). The translational and rotational variables describe the position and orientation of a component of a surgical system (e.g., end effector 604) with respect to a given reference Cartesian frame or similar reference frame (e.g., a spherical coordinate system). As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

A pivoting motion may include pitch movement about a first axis of wrist 606 (e.g., X-axis), yaw movement about a second axis of wrist 606 (e.g., Y-axis), and combinations thereof to allow for 360° rotational movement of end effector 604 about wrist 606. In other applications, the pivoting motion can be limited to movement (rotation) in a single plane (e.g., only pitch movement about the first axis of wrist 606 or only yaw movement about second axis of wrist 606).

Referring again to FIG. 6, surgical tool 600 may include a plurality of drive cables (obscured in FIG. 6) that form part of a cable driven motion system, described in more detail below, that is configured to facilitate operation and articulation (movement) of end effector 604 relative to elongate shaft 602. For example, selectively moving one or more of the drive cables can actuate end effector 604 and thereby collapse jaw members 610 and 612 toward each other. Moreover, moving one or more of the drive cables can also transition end effector 604 between an unarticulated position and an articulated position. End effector 604 is depicted in FIG. 6 in the unarticulated position where longitudinal axis $A_2$ of end effector 604 is substantially aligned with longitudinal axis $A_1$ of elongate shaft 602, such that end effector 604 is at a substantially zero angle relative to elongate shaft 602. In the articulated position, longitudinal axes $A_1$ and $A_2$ are angularly offset from each other such that end effector 604 is at a non-zero angle relative to elongate shaft 602.

Figure 8:
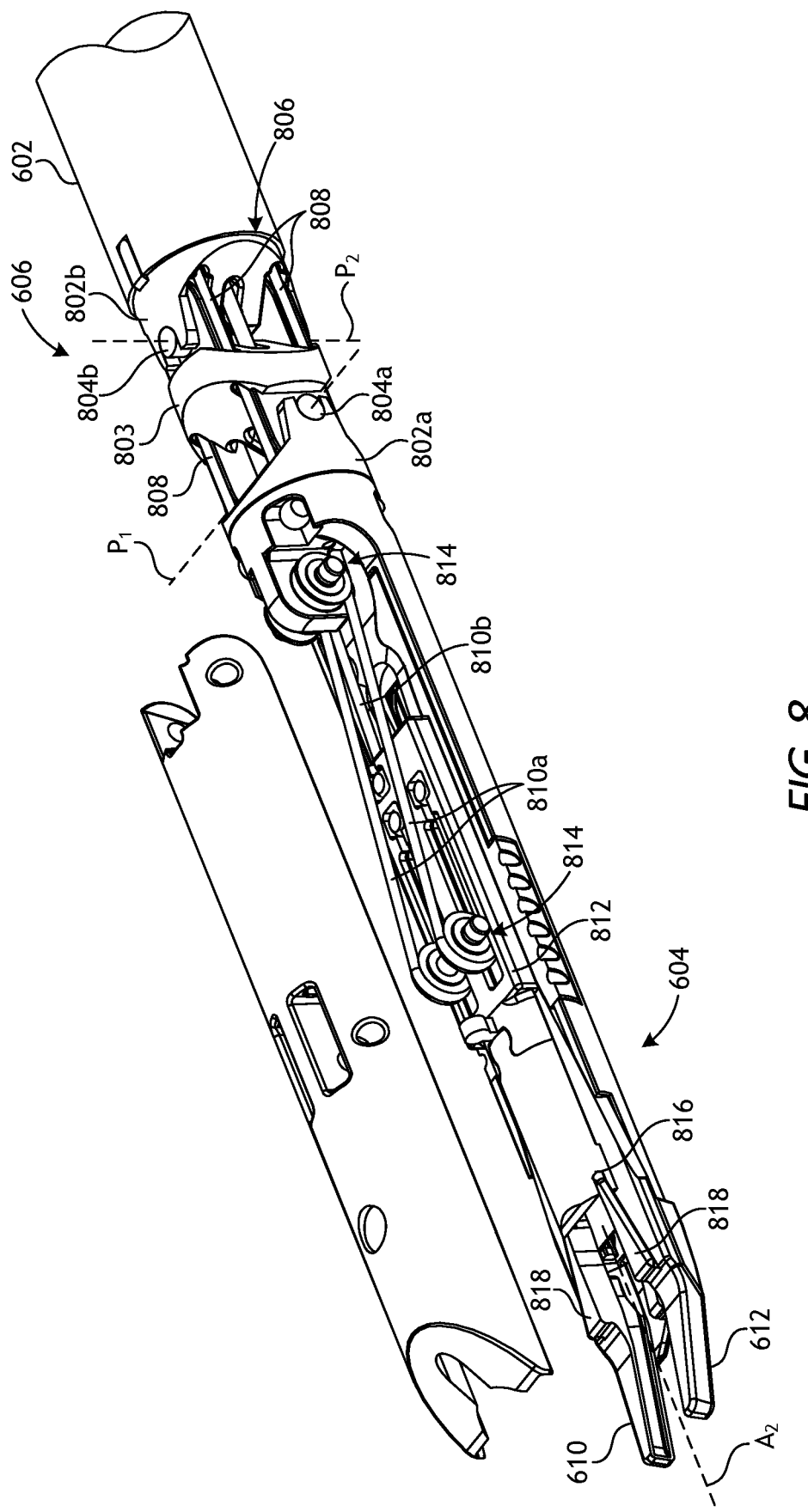
FIG. 8 is an enlarged, partially exploded isometric view of the distal end of the illustrative surgical tool of FIG. 6.

FIG. 8 is an enlarged isometric view of the distal end of illustrative surgical tool 600 of FIG. 6. More specifically, FIG. 8 depicts an enlarged and partially exploded view of end effector 604 and wrist 606. Wrist 606 operatively couples end effector 604 to elongate shaft 602. To achieve operable coupling, wrist 606 includes distal clevis 802a, proximal clevis 802b, and spacer 803 interposed between distal clevis 802a and proximal clevis 802b. End effector 604 is coupled to distal clevis 802a, and distal clevis 802a is rotatably mounted to spacer 803 at first axle 804a. Spacer 803 is rotatably mounted to proximal clevis 802b at second axle 804b, and proximal clevis 802b is coupled to distal end 806 of elongate shaft 602.

Wrist 606 provides first pivot axis $P_1$ that extends through first axle 804a and second pivot axis $P_2$ that extends through second axle 804b. First pivot axis $P_1$ is substantially perpendicular (orthogonal) to longitudinal axis $A_2$ of end effector 604, and second pivot axis $P_2$ is substantially perpendicular (orthogonal) to both longitudinal axis $A_2$ and first pivot axis $P_1$. Movement about first pivot axis $P_1$ provides "pitch" articulation of end effector 604, and movement about second pivot axis $P_2$ provides "yaw" articulation of end effector 604.

A plurality of drive cables 808 extend longitudinally within elongate shaft 602, pass through wrist 606 and are operably coupled to a component of end effector 604. Drive cables 808 form part of the cable driven motion system referenced in brief above, and may be referred to herein and otherwise be characterized as cables, bands, lines, cords, wires, ropes, strings, twisted strings, elongate members, and the like. Drive cables 808 may be made from a variety of materials including, but not limited to, metal (e.g., tungsten, stainless steel, and the like) or a polymer.

Drive cables 808 extend proximally from end effector 604 to drive housing 608 (FIG. 6), where they are operatively coupled to various actuation mechanisms or devices housed (contained) therein to facilitate longitudinal movement (translation) of drive cables 808. Selective actuation of drive cables 808 may cause end effector 604 to articulate (pivot) relative to elongate shaft 602. Moving a given drive cable 808 constitutes applying tension (i.e., a pull force) to the given drive cable 808 in a proximal direction, which causes the given drive cable 808 to translate proximally and thereby cause end effector 604 to move (articulate) relative to elongate shaft 602.

One or more actuation cables, shown as first actuation cables 810a and second actuation cables 810b, may also extend longitudinally within elongate shaft 602 and pass through wrist 606, where they are operably coupled to a component of end effector 604. First and second actuation cables 810a and 810b may be similar in nature to drive cables 808 and also form part of the above-referenced cable driven motion system. Selectively actuating first and second actuation cables 810a and 810b causes end effector 604 to actuate, such as collapsing jaw members 610 and 612 to crimp an interposed surgical clip (not shown).

More specifically, first and second actuation cables 810a and 810b may be operatively coupled to cam 812 that is slidably engageable with jaw members 610 and 612. One or more pulleys 814 may receive and redirect first actuation cables 810a for engagement with cam 812. As such, longitudinal movement of first actuation cables 810a correspondingly moves cam 812 distally relative to jaw members 610 and 612. The distal end of cam 812 includes a tapering recess or camming channel 816 formed therein for slidably receiving corresponding cam tracks 818 provided by jaw members 610 and 612. As cam 812 is advanced distally, camming channel 816 pushes (collapses) jaw members 610 and 612 toward one another, thereby crimping an interposed surgical clip (not shown). Longitudinal movement of second actuation cables 810b (one shown) may pull cam 812 proximally, thereby allowing jaw members 610 and 612 to open again to receive another surgical clip.

Although not expressly depicted in FIG. 8, an assembly including, for example, a feedbar, a feeder shoe, and a clip track may be included at or near end effector 604 to facilitate feeding of surgical clips into jaw members 610 and 612. These elements may be similar to those shown in surgical tool 200 and described in more detail hereinabove. In some embodiments, the feedbar (or a connecting member) may be flexible and extend through wrist 606.

Figure 9:
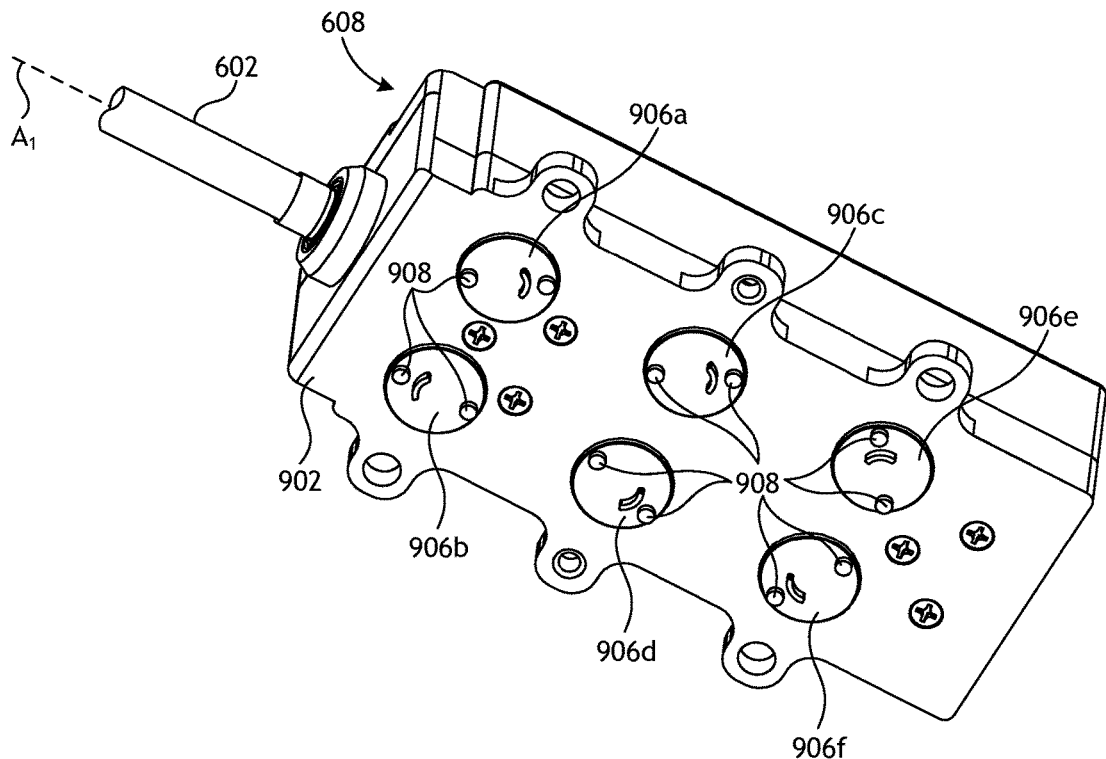
FIG. 9 is a bottom view of the drive housing of the illustrative surgical tool of FIG. 6.

FIG. 9 is a bottom view of drive housing 608 of illustrative surgical tool 600, according to one or more embodiments. As illustrated, drive housing 608 may include tool mounting interface 902 used to operatively couple drive housing 608 to a robotic manipulator. Without limitation, tool mounting interface 902 may mechanically, magnetically, and/or electrically couple drive housing 608 to the robotic manipulator.

Tool mounting interface 902 further includes and supports a plurality of drive inputs, shown in FIG. 9 as drive inputs 906a, 906b, 906c, 906d, 906e, and 906f. Each drive input 906a-f may comprise a rotatable disc configured to align with and couple to a corresponding input actuator (not shown) of a corresponding robotic manipulator, similar to those described above for surgical tool 200. Each drive input 906a-f may further provide or define one or more surface features 908 configured to align with mating features provided on the corresponding input actuator. The surface features 908 can include, for example, various protrusions and/or indentations that facilitate a mating engagement.

In some embodiments, actuation of first drive input 906a may control rotation of elongate shaft 602 about longitudinal axis $A_1$. Depending on the rotational direction of first drive input 906a, elongate shaft 602 may be rotated clockwise or counterclockwise. Rotation capabilities of elongate shaft 602 optionally may be omitted in some embodiments. In some embodiments, selective actuation of second and/or third drive inputs 906b and 906c may cause movement (axial translation) of first and/or second actuation cables 810a and 810b (FIG. 8), which correspondingly may cause cam 812 (FIG. 8) to move and crimp an interposed surgical clip between jaw members 610 and 612, as generally described above. In some embodiments, actuation of fourth drive input 906d may feed a surgical clip into interposition between jaw members 610 and 612 (e.g., by longitudinally translating and retracting a feedbar). In some embodiments, actuation of fifth and sixth drive inputs 906e and 906f may cause movement (axial translation) of drive cables 808 (FIG. 8) to result in articulation of end effector 604. Each of drive inputs 906a-f may be actuated independently based on user inputs communicated to a robotic manipulator coupled to tool mounting interface 902. The user inputs may be received via a computer system incorporated into the robotic surgical system.

Figure 10:
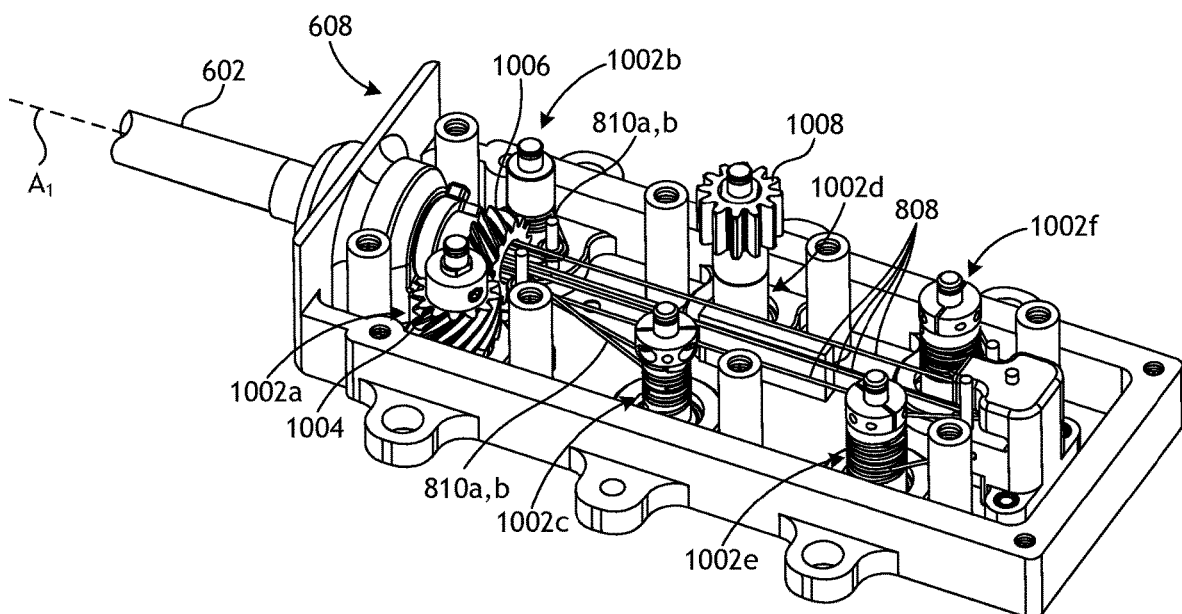
FIG. 10 is an isometric exposed view of the interior of the drive housing of the illustrative surgical tool of FIG. 6.

FIG. 10 is an isometric exposed view of the interior of drive housing 608 of illustrative surgical tool 600, according to one or more embodiments. Several component parts that may otherwise be contained within drive housing 608 are not shown in FIG. 10 to allow for clearer viewing of the depicted component parts and to facilitate discussion thereof.

As illustrated in FIG. 10, drive housing 608 contains first capstan 1002a, which is operatively coupled to or extends from first drive input 906a (FIG. 9), such that actuation of first drive input 906a results in rotation of first capstan 1002a. Helical drive gear 1004 is coupled to or forms part of first capstan 1002a and is configured to interact with helical driven gear 1006 that is operatively coupled to elongate shaft 602, such that rotation of driven gear 1006 may correspondingly rotate elongate shaft 602. Accordingly, rotation of helical drive gear 1004 (via actuation of first drive input 906a) drives driven gear 1006 and thereby affects rotation of elongate shaft 602 about longitudinal axis $A_1$.

When rotation of elongate shaft 602 is unnecessary or undesired in alternate configurations of surgical tool 600, the components engageable with first drive input 906a may be configured differently. For example, first capstan 1002a may be configured to translate a cable longitudinally within elongate shaft 602 instead of promoting rotation of elongate shaft 602 as depicted. The cable may aid in actuating other various components within end effector 604.

Drive housing 608 also includes second and third capstans 1002b and 1002c operatively coupled to or extending from second and third drive inputs 906b and 906c (FIG. 9), respectively, such that actuation of second and/or third drive inputs 906b and 906c results in rotation of second and/or third capstans 1002b and 1002c. Second and third capstans 1002b and 1002c comprise capstan pulleys operatively coupled to first and second actuation cables 810a and 810b (FIG. 8), respectively, such that rotation of either second capstan 1002b or third capstan 1002c actuates (longitudinally moves) a corresponding one of first actuation cable 810a or second actuation cable 810b. Accordingly, selective rotation of second and/or third capstans 1002b and 1002c via actuation of second and/or third drive inputs 906b and 906c, respectively, causes movement (axial translation) of first and/or second actuation cables 810a and 810b, resulting in movement of cam 812 and crimping of an interposed surgical clip between jaw members 610 and 612.

Drive housing 608 further includes fourth capstan 1002d, which is operatively coupled to or extends from fourth drive input 906d (FIG. 9), such that actuation of fourth drive input 906d results in rotation of fourth capstan 1002d. Spur gear 1008 is coupled to or forms part of fourth capstan 1002d and is configured to mesh and interact with a rack gear (not shown) also contained within drive housing 608. The rack gear may be operatively coupled to a feedbar (or another connecting member), which facilitates operation of a feeder shoe and associated clip track to feed surgical clips into jaw members 610 and 612 (FIGS. 6 and 8). Accordingly, rotation of spur gear 1008 (via actuation of fourth drive input 906d) may control the feedbar and thereby facilitate loading of surgical clips into jaw members 610 and 612 as desired.

Drive housing 608 further includes fifth and sixth capstans 1002e and 1002f operatively coupled to or extending from fifth and sixth drive inputs 906e and 906f (FIG. 9), respectively, such that actuation of fifth and sixth drive inputs 906e and 906f results in rotation of fifth and sixth capstans 1002e and 1002f. Fifth and sixth capstans 1002e and 1002f each comprise capstan pulleys operatively coupled to drive cables 808 (FIG. 8), such that rotation of fifth and/or sixth capstans 1002e and 1002f actuates (longitudinally moves) a corresponding one of drive cables 808. Accordingly, selective rotation of fifth and/or sixth capstans 1002e and 1002f via actuation of fifth and/or sixth drive inputs 906e and 906f, respectively, may affect movement (axial translation) of drive cables 808 and thereby articulate (pivot) end effector 604 relative to elongate shaft 602.

The principles and features of the present disclosure may be incorporated within surgical tools 200 and 600 described hereinabove, as well as within similar surgical tools, to facilitate feeding and more efficient packing of surgical clips in surgical clip appliers, including robotic clip appliers, laparoscopic clip appliers, endoscopic clip appliers, and similar surgical tools, particularly surgical tools incorporating an articulable wrist. As will be appreciated by one having ordinary skill in the art and the benefit of the present disclosure, some or all of the principles and features of surgical tools 200 and 600 may be modified to incorporate the various surgical clip feeding and packing features described hereinafter. Accordingly, example surgical tools incorporating the principles, features and benefits of the present disclosure may incorporate any combination of geared actuators, capstan pulleys, cable actuators, feedbars, cams, and similar elements, such as those described above in reference to FIGS. 2-10, without departing from the scope of the present disclosure. Such components may be operably connected to and/or contained within an end effector incorporating the principles described hereinafter.

According to various embodiments, end effectors of surgical tools of the present disclosure may house multiple surgical clips at a location distal to a wrist or similar articulation joint (e.g., wrist 606 in FIG. 6) used to promote articulation of the end effector, such as a surgical clip applier. That is, surgical tools and end effectors of the present disclosure may incorporate (store) the surgical clips on a side of the wrist that is closer to the jaw members of a surgical clip applier rather than nearer to the drive housing or other location of engagement of a surgical tool. As such, end effectors of the present disclosure avoid the issue of having to transport (convey) surgical clips through the wrist to affect clip feeding to the jaw members of a surgical clip applier. It is to be appreciated, however, that the principles of the present disclosure may be similarly employed within surgical tools that do not incorporate a wrist or similar articulation joint, without departing from the scope of the disclosure.

In addition, the surgical clips may be housed with efficient clip packing (arrangement) in the region distal to the wrist, thereby not significantly impacting the diameter or length of the end effector and undesirably impacting articulation accuracy thereof. More particularly, the surgical clips are disposed in the end effectors of the present disclosure such that the surgical clips can be packed more closely within a given longitudinal distance (space) compared to crown-to-tail packing in a single-layer (coplanar) packing configuration. As such, the various embodiments of the present disclosure provide increased surgical clip packing density within the end effector of the surgical tool. Various surgical clip packing arrangements suitable for use in the present disclosure may include those in which the surgical clips are packed in abutted stacks (i.e., a first plurality of surgical clips is disposed in a first layer in a crown-to-tail packing fashion and at least a second plurality of surgical clips is disposed in a second layer situated upon the first layer) or at an angled packing arrangement, both of which may afford denser packing of the surgical clips.

In one suitable packing configuration, the surgical clips may be arranged both longitudinally and radially (i.e., arranged in at least two layers) with respect to a longitudinal axis of the end effector. More specifically, in such embodiments, a first plurality of surgical clips may be arranged in a crown-to-tail fashion in a first layer and extend longitudinally within the end effector. At least a second plurality of surgical clips, also arranged in a crown-to-tail fashion and extending longitudinally in a second layer, may overlay at least a portion of the first plurality of surgical clips, thereby providing a plurality of stacks of surgical clips, wherein the stacks also extend longitudinally within the end effector and contain surgical clips that are abutted crown-to-tail in adjacent stacks. According to various embodiments, each layer may contain two or more surgical clips or, equivalently, two or more stacks may be abutted longitudinally against one another. Within a given stack, the surgical clips may overlay one another in a crown-to-crown and tail-to-tail fashion. Provided that the number of surgical clips within each stack is kept sufficiently small, the stacks may be accommodated in the available radial space distal to the wrist within the end effector. According to various embodiments, the number of surgical clips within each stack may be chosen such that the stack height is less than the crown-to-tail length of a given surgical clip accommodated therein.

In another illustrative packing configuration, the surgical clips may be arranged in series at a non-zero angle with respect to the longitudinal axis of the end effector, such that a more distal surgical clip partially overlays a more proximal surgical clip. In such surgical clip packing configurations, the surgical clips are disposed in a partially "nested" configuration at a non-zero angle with respect to the longitudinal axis, with the crown of the more distal surgical clip overlaying the tail (legs) of the more proximal surgical clip. The angle at which the surgical clips are packed may be selected to increase the number of surgical clips arranged within a given longitudinal distance (as compared to coplanar crown-to-tail packing) while not increasing the radial profile of the end effector.

Moreover, according to some embodiments of the present disclosure, two sources (groups) of surgical clips may be disposed in opposite hemispheres of the end effector, as defined with respect to the longitudinal axis, thereby allowing the number of available surgical clips to be increased still further. The surgical clips in each group may be arranged according to the packing configurations referenced above, particularly the angled packing configuration. The size, number, and/or type of surgical clips in each group may be the same or different, which may be advantageous upon encountering particular conditions during a surgical procedure (e.g., an unexpected size of a vessel or duct). Furthermore, by having two sources of surgical clips that are available for independent dispensation from a single surgical tool, a failsafe against unforeseen failure of one source during a surgical procedure may be provided.

FIGS. 11-15 are isometric views of end effector 1100 of the present disclosure, in which surgical clip feeder 1102 is packed both longitudinally and radially with surgical clips 1110a-f (i.e., in abutted surgical clip stacks). As depicted, FIGS. 11-15 show the portion of end effector 1100 distal to a wrist (not shown in FIGS. 11-15), where surgical clip feeder 1102 is located distal to the wrist. It is to be appreciated that end effector 1100 may be operatively coupled to a wrist similar to wrist 606 (FIG. 6), as well as other previously described features and components suitable for articulating, rotating and/or actuating the components comprising end effector 1100. As such, for example, it is to be appreciated that drive inputs and capstans similar to drive inputs 906a-f (FIG. 9) and capstans 1002a-f (FIG. 10) and their associated features may be in communication with one or more of the various components depicted in FIGS. 11-15 in order to affect operation thereof. Moreover, it is to be further appreciated that surgical clip feeder 1102 may be employed in the end effector of non-wristed surgical tools as well.

Figure 11:
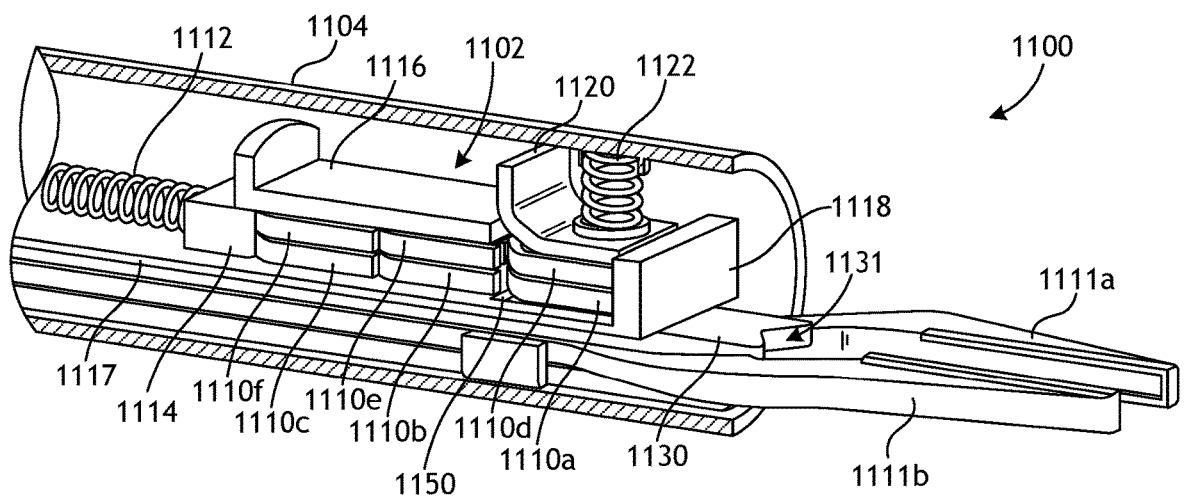
FIGS. 11-15 are isometric views of a first end effector of the present disclosure.

As shown in FIG. 11, surgical clip feeder 1102 is arranged within housing 1104 and is positioned proximal to jaw members 1111a and 1111b. Surgical clip feeder 1102 is loaded with surgical clips 1110a-c packed in a first layer and surgical clips 1110d-f packed in a second layer. Within the first layer and the second layer, corresponding surgical clips 1110a-c and surgical clips 1110d-f may be packed in a crown-to-tail fashion. Alternately, surgical clips 1110a and 1110d may be considered to constitute a first stack, surgical clips 1110b and 1110e may be considered to constitute a second stack, and surgical clips 1110c and 1110f may be considered to constitute a third stack, where the first, second, and third stacks are longitudinally abutted against one another.

Depending on their location within surgical clip feeder 1102, surgical clips 1110a-f may be movable longitudinally and/or radially in sequence within surgical clip feeder 1102 to promote their dispensation therefrom, as described in further detail below. To this end, surgical clip feeder 1102 includes upper retainer plate 1116, lower retainer plate 1117, and forward stop 1118 to aid in maintaining surgical clips 1110a-f therein until their dispensation is desired.

Surgical clip feeder 1102 may include feed spring 1112 configured to apply a longitudinal (axial) load to facilitate distal advancement of at least a portion of the stacks of surgical clips 1110a-f during use. Feed spring 1112 is operably connected to pusher plate 1114, which may be directly or indirectly abutted against the proximal-most stack of surgical clips (i.e., surgical clips 1110c and 1110f), and transfers an longitudinal (axial) load thereto for pushing the stacks distally. In the depicted configuration, surgical clips 1110a and 1110d (i.e., the first stack) are already longitudinally positioned for deployment from surgical clip feeder 1102 and do not undergo distal advancement during use. Once surgical clips 1110a and 1110d have been discharged from surgical clip feeder 1102, as described hereinafter, feed spring 1112 may urge remaining surgical clips 1110b,c,e,f distally. Approaches other than spring-based biasing for distally advancing surgical clips 1110b,c,e,f within surgical clip feeder 1102 also reside within the scope of the present disclosure and are discussed hereinbelow.

Surgical clip feeder 1102 also includes spring shoe 1120 that is configured to radially engage the distal-most stack of surgical clips (i.e., surgical clips 1110a and 1110d in FIG. 11). The face of spring shoe 1120 that engages the distal-most stack of surgical clips may bear certain structural and operational similarities to the shoes described in U.S. Pat. No. 8,801,732, which is incorporated herein by reference in its entirety. Advantageously, spring shoe 1120 may radially advance the distal-most stack of surgical clips radially without the need for a separate drive mechanism extending from a drive housing. Biasing member 1122 interposes spring shoe 1120 and an inner wall of housing 1104 to apply a radial load onto the distal-most stack of surgical clips via spring shoe 1120. In the illustrated configuration, biasing member 1122 is depicted as a compression spring, but may alternatively comprise a series of Belleville washers, a hydraulic or pneumatic piston, a magnet arrangement, or any other type of biasing mechanism capable of applying a radial load to the clip stack below spring shoe 1120. Spring shoe 1120 extends longitudinally between upper retainer plate 1116 and forward stop 1118 and is configured to translate radially therebetween during operation. The radial load transferred by spring shoe 1120 promotes sequential clip ejection from surgical clip feeder 1102 through aperture 1150 defined in lower retainer plate 1117 and into clip track 1131, as described hereinafter, for subsequent clip loading between jaw members 1111a and 1111b.

End effector 1100 further includes feedbar 1130, which is adapted to translate longitudinally within clip track 1131 relative to surgical clip feeder 1102 based upon an input from a corresponding drive housing (not shown). According to various embodiments, feedbar 1130 or a component thereof may extend through the wrist (not shown) in order to aid in positioning surgical clips 1110a-f between jaw members 1111a and 1111b during use. In other embodiments, however, feedbar 1130 may be operatively coupled to a cable-driven worm gear and associated drive cable(s) that move as the worm gear extends and retracts the drive cable(s) through the wrist.

As depicted in FIG. 11, feedbar 1130 is extended beyond forward stop 1118 within clip track 1131 and blocks ejection of the distal-most stack of surgical clips from surgical clip feeder 1102. Specifically, feedbar 1130 blocks (occludes) aperture 1150 extending through lower retainer plate 1117, through which individual surgical clips 1110a-f are ejected one at a time into clip track 1131.

Figure 12:
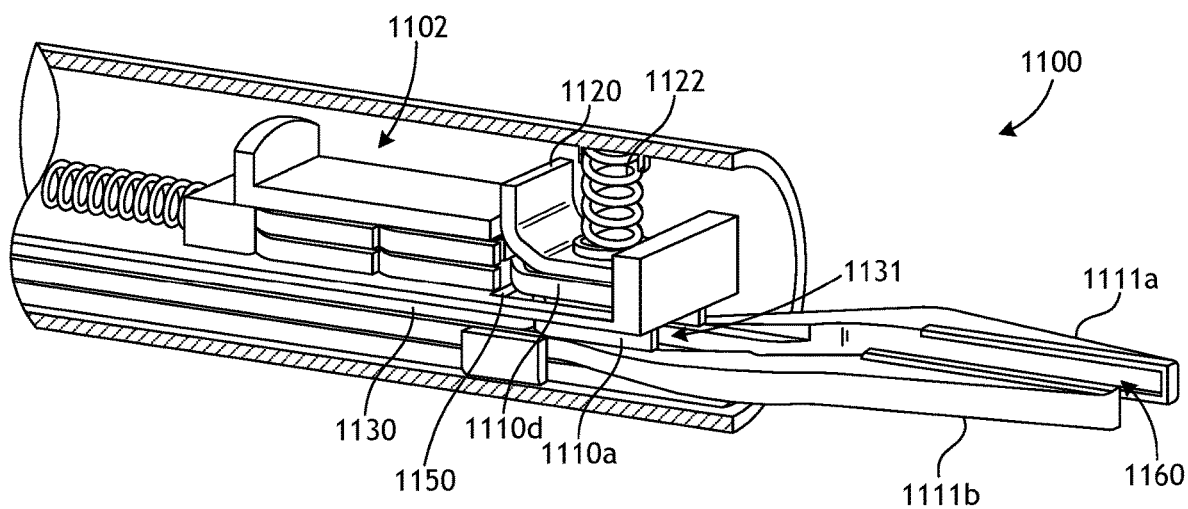

As shown in FIG. 12, feedbar 1130 has been retracted proximally relative to surgical clip feeder 1102 such that aperture 1150 is no longer occluded by feedbar 1130. Once aperture 1150 is exposed, spring shoe 1120 may then urge the distal-most clip stack (i.e., surgical clips 1110a and 1110d) downward under influence of the radial load. As shown, surgical clip 1110a is ejected from surgical clip feeder 1102 into clip track 1131. The depth of clip track 1131 is sufficient to only receive a single surgical clip at a time, thus preventing surgical clip 1110d from also entering clip track 1131. That is, surgical clip 1110a blocks the ejection of surgical clip 1110d from surgical clip feeder 1102 into clip track 1131. Instead, surgical clip 1110d remains within surgical clip feeder 1102, occupying the location previously held by surgical clip 1110a.

Following the ejection of surgical clip 1110a into clip track 1131, feedbar 1130 may then be actuated and translated distally to engage and urge surgical clip 1110a forward into interposition between jaw members 1111a and 1111b. According to some embodiments, jaw members 1111a and 1111b may each include grooves 1160 (one shown in FIG. 12), each sized to receive the legs of surgical clip 1110a, and thereby aid in maintaining surgical clip 1110a therebetween. In other embodiments, however, grooves 1160 may be omitted, with jaw members 1111a and 1111b instead applying a sufficient lateral load on incoming surgical clip 1110a to facilitate retention until crimping.

Figure 13:
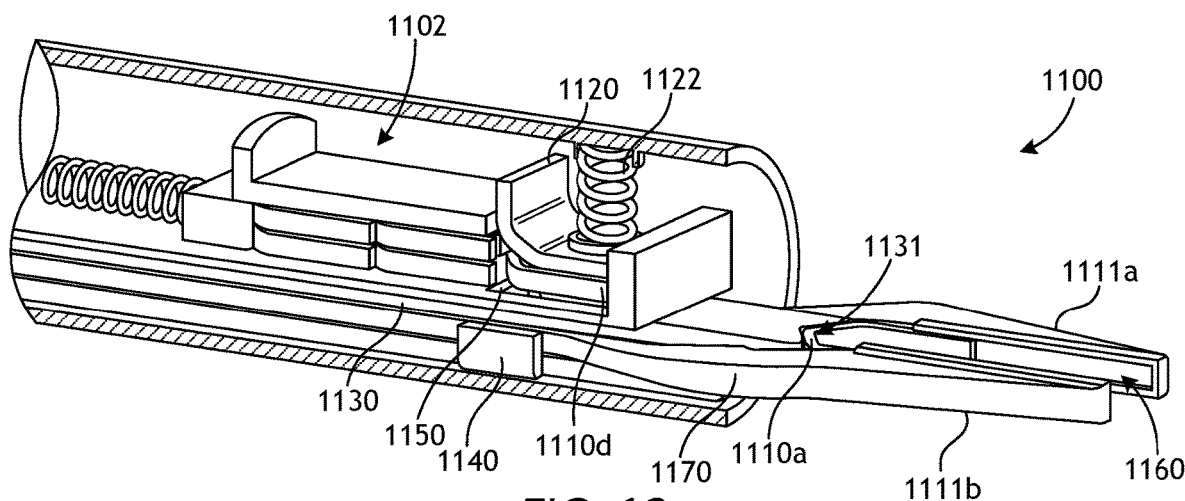

FIG. 13 shows feedbar 1130 in the process of distally advancing surgical clip 1110a into interposition between jaw members 1111a and 1111b, specifically within grooves 1160 defined on jaw members 1111a and 1111b. Feedbar 1130 again occludes aperture 1150 in lower retainer plate 1117 when positioning surgical clip 1110a between jaw members 1111a and 1111b, thereby precluding release of surgical clip 1110d from surgical clip feeder 1102 into clip track 1131. Once surgical clip 1110a has been properly positioned between jaw members 1111a and 1111b and feedbar 1130 has been withdrawn distally, camming mechanism 1140 may be actuated and translated distally to engage cam tracks 1170 (one visible in FIG. 13) and thereby urge jaw members 1111a and 1111b toward one another to crimp surgical clip 1110a. As depicted, cam tracks 1170 comprise opposing lobes defined on an outer surface of jaw members 1111a and 1111b, but may alternatively comprise other types of camming configurations known in the art without departing from the scope of the present disclosure.

Jaw members 1111a and 1111b may be naturally biased to an open position to receive surgical clip 1110a and subsequent surgical clips. Consequently, distal withdrawal of camming mechanism 1140 allows jaw members 1111a and 1111b to return to the open position or otherwise move away from one another to release surgical clip 1110a in a crimped state.

Figure 14:
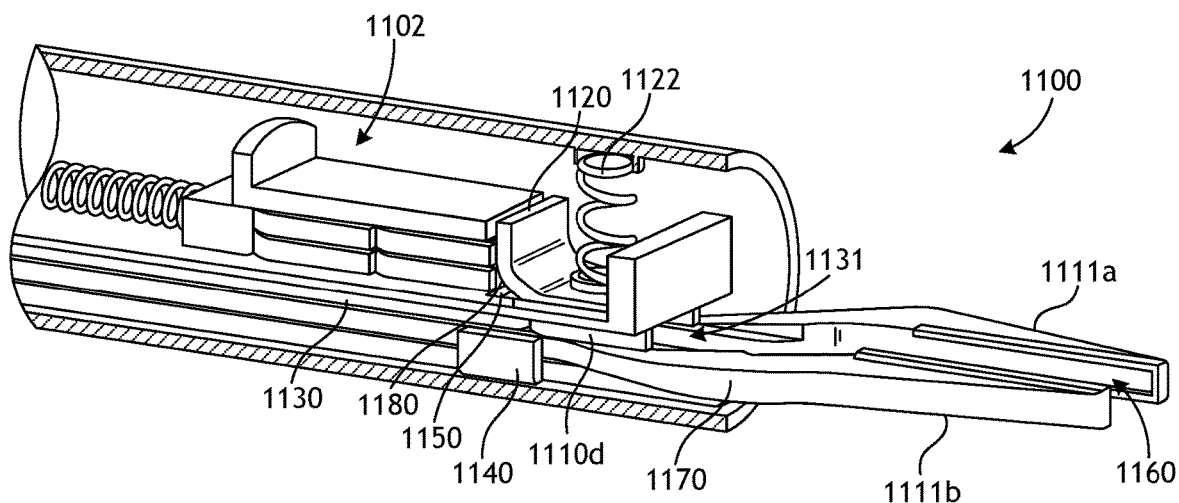

Following crimping and release of surgical clip 1110a from jaw members 1111a and 1111b, feedbar 1130 may be retracted proximally to release surgical clip 1110d from surgical clip feeder 1102, as shown in FIG. 14. Specifically, feedbar 1130 may be retracted proximally into a position similar to that shown in FIG. 12, thereby once again exposing aperture 1150. Once aperture 1150 is exposed, surgical clip 1110d may be ejected into clip track 1131 under influence of the radial biasing force provided by spring shoe 1120. Surgical clip 1110d may then be advanced distally, positioned between jaw members 1111a and 1111b, and crimped as generally described above with reference to surgical clip 1110a in FIGS. 12 and 13.

Figure 15:
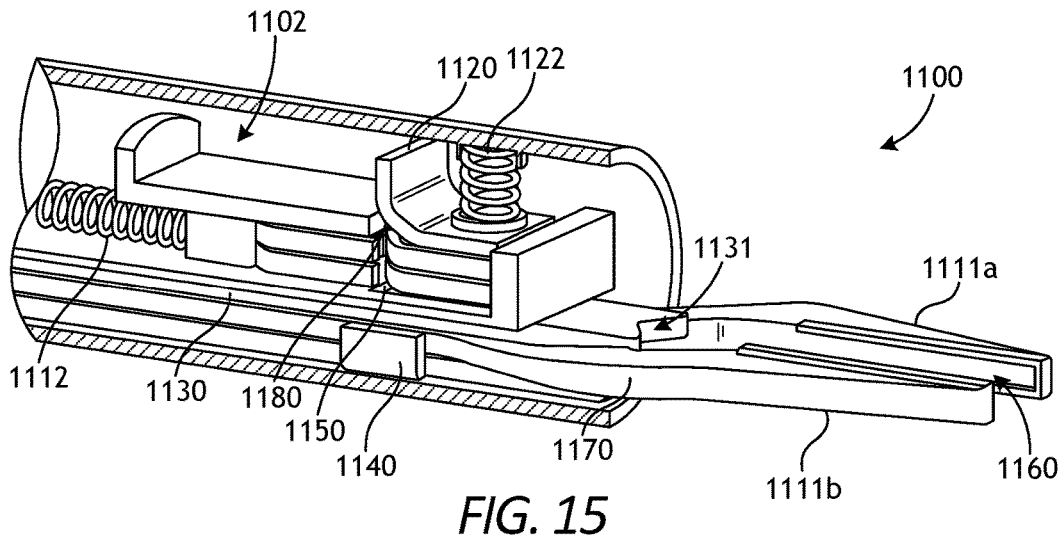

Once the distal-most stack of surgical clips (i.e., surgical clips 1110a and 1110d) has been dispensed from surgical clip feeder 1102, the remaining stacks may be advanced distally for subsequent dispensation. FIG. 15 depicts the remaining stacks of surgical clips being advanced distally in preparation for discharge into clip track 1131. More specifically, following release of surgical clip 1110d from surgical clip feeder 1102 into clip track 1131, the remaining two stacks of surgical clips (i.e., surgical clips 1110b,d,e,f) may be advanced within surgical clip feeder 1102 via the longitudinal (axial) biasing force supplied by feed spring 1112, with surgical clip 1110b becoming queued for next dispensation, followed by surgical clip 1110e, in a manner identical to that described above for surgical clips 1110a and 1110d.

As the remaining stacks of surgical clips advance distally within surgical clip feeder 1102, the distal-most remaining stack engages and urges spring shoe 1120 radially outward (upward), thereby clearing space for the incoming stack above aperture 1150. In some embodiments, and as illustrated, spring shoe 1120 may provide ramped (angled) surface 1180 (see FIG. 14) that is engageable by the distal-most stack once spring shoe 1120 has extended to complete deployment of the previous stack. Ramped surface 1180 allows the advancing stacks to impel spring shoe 1120 radially outward as the stacks continue to advance distally until engaging forward stop 1118. It is to be understood that spring shoe 1120 may have a different shape than that depicted, while remaining capable of radial retraction upon interacting with the incoming stack. Once radially retracted, spring shoe 1120 is poised to sequentially dispense surgical clips 1110b and 1110e into clip track 1131 after feedbar 1130 is proximally withdrawn, as described above. Similarly, distal advancement and proximal withdrawal of feedbar 1130 and camming mechanism 1140 may then be repeated as described above until the supply of surgical clips 1110a-f is exhausted.

Although FIGS. 11-15 have depicted biased distal advancement of surgical clips 1110a-f via feed spring 1112, it is to be appreciated that alternative mechanisms may also be used to selectively advance surgical clips 1110a-f, such as those incorporating electrical, mechanical, electromechanical, hydraulic, pneumatic, or magnetic biasing principles. Moreover, in alternative embodiments, non-biased distal advancement of surgical clips 1110a-f may take place. In some embodiments, for example, feed spring 1112 may be replaced with a push rod or like mechanism that may be actuated directly from a drive housing or via a geared assembly or the like. In embodiments employing a geared assembly, for example, the push rod may be operatively coupled to a cable-driven worm gear positioned adjacent to surgical clip feeder 1102, and associated drive cable(s) that move the worm gear may extend thereto from a drive housing and potentially through a wrist.

It is to be further appreciated that while surgical clip feeder 1102 has been depicted as containing six surgical clips 1110a-f, arranged in three stacks, these numbers are merely illustrative. In some embodiments, surgical clip feeder 1102 may contain multiple stacks of surgical clips arranged serially and having between two and about six surgical clips in each stack. The number of surgical clips in each stack may be dictated by the amount of radial space available within end effector 1100, for example. Similarly, it can be appreciated that more or less than three stacks (i.e., at least two stacks) may be present within surgical clip feeder 1102 without departing from the scope of the disclosure.

Moreover, according to some embodiments, surgical clips 1110a-f or another suitable number of surgical clips may be added to end effector 1100 in a cartridge, magazine, or similar structure.

Other end effectors of the present disclosure may include at least one surgical clip feeder in which the surgical clips are packed (arranged) at a non-zero angle with respect to a longitudinal axis of the end effector. As discussed in brief above, overlaying the surgical clips at an angle affords a more compact packing arrangement than does crown-to-tail packing in a single plane. As such, angled clip packing allows more surgical clips to be housed in the same longitudinal space in a given end effector or, alternately, for the longitudinal space distal to the wrist in an end effector to be decreased (shortened) while still housing sufficient surgical clips to conduct a given surgical procedure. Furthermore, according to some embodiments, end effectors having surgical clips packed at a non-zero angle may include the surgical clips within two surgical clip feeders provided in opposite hemispheres of the end effector, and which are capable of independent actuation to promote surgical clip dispensation therefrom.

FIGS. 16-20 show various views of end effector 1500 containing an angled packing arrangement of surgical clips within hemispherically positioned surgical clip feeders. It is to be appreciated that end effector 1500 may be operatively coupled to a wrist similar to wrist 606 (FIG. 6), as well as other previously described features or components suitable for articulating, rotating and/or actuating the components comprising end effector 1500. As such, for example, it is to be appreciated that drive inputs and capstans similar to drive inputs 906a-f (FIG. 9) and capstans 1002a-f (FIG. 10) and their associated features may be in communication with one or more of the various components depicted in FIGS. 16-20 in order to promote operation thereof.

Figure 16:
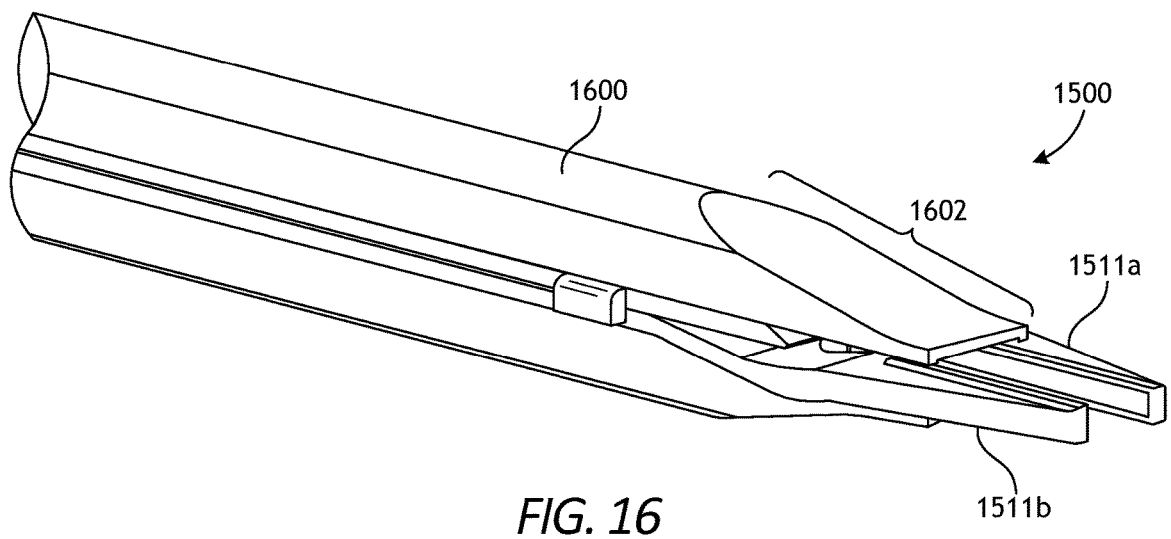
FIGS. 16-18 are isometric views of a second end effector of the present disclosure.

FIG. 16 shows an isometric view of the exterior of end effector 1500, which includes housing 1600. Housing 1600 may function as a shroud to cover the internal components of end effector 1500, which are described in further detail hereinafter. Moreover, tapered section 1602 at a distal end of housing 1600 may include an internally tapered surface to aid in guiding surgical clips into interposition between jaw members 1511a and 1511b, as also described hereinafter. Further, the inner surface (internally tapered surface) of housing 1600 within tapered section 1602 may define channels (not visible in FIG. 16) that the surgical clips may traverse prior to becoming interposed between jaw members 1511a and 1511b.

Figure 17:
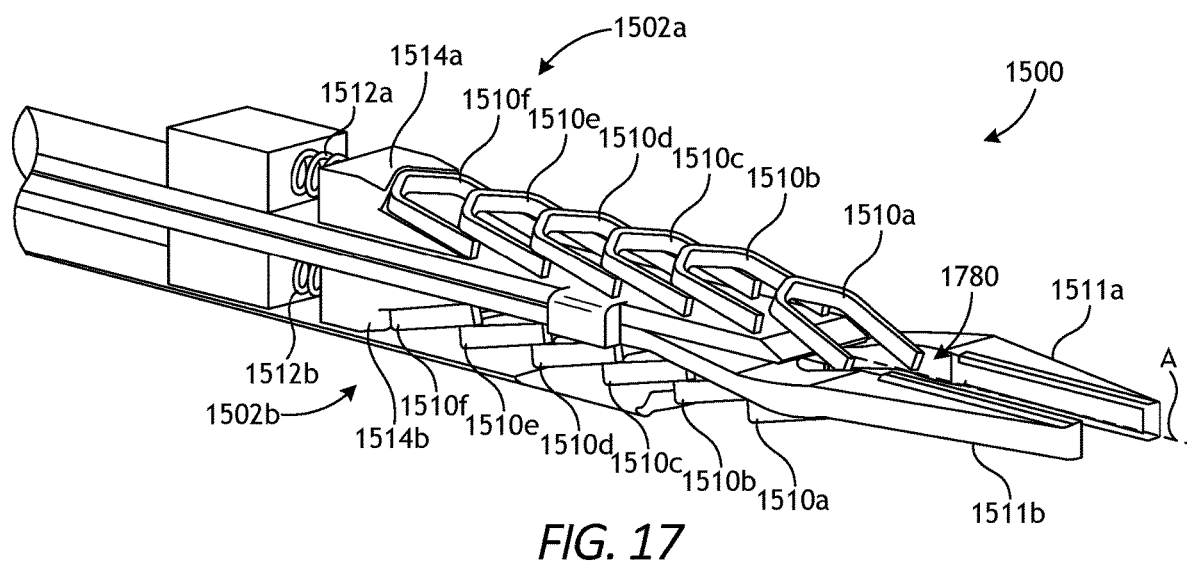
Figure 18:
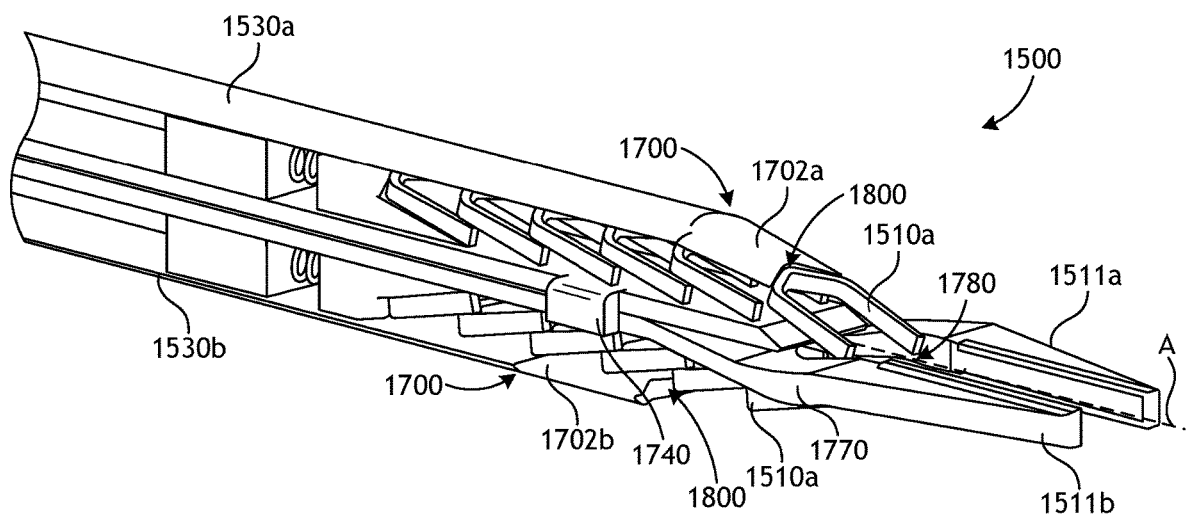

FIGS. 17 and 18 are exposed isometric views of end effector 1500, in which housing 1600 (FIG. 16) has been removed to show various internal components. As depicted in FIG. 17, end effector 1500 may include first surgical clip feeder 1502a and second clip feeder 1502b, each loaded with multiple surgical clips 1510a-f in an angled packing arrangement with respect to longitudinal axis A. Surgical clip feeders 1502a and 1502b are positioned in opposite hemispheres (sides) of end effector 1500. While two surgical clip feeders 1502a and 1502b are shown in end effector 1500, it is to be appreciated that the principles of the present disclosure also apply to end effectors containing a single surgical clip feeder likewise featuring an angled packing arrangement of surgical clips.

It is to be further appreciated that the depiction of surgical clip feeders 1502a and 1502b as having six surgical clips 1510a-f is for purposes of illustration only, as more or less than six surgical clips may be present in other various embodiments. The available longitudinal space within end effector 1500, for example, may dictate the actual number of surgical clips that may be located within housing 1600 (FIG. 16).

Moreover, the non-zero packing angle depicted in FIGS. 17 and 18 between surgical clips 1510a-f with respect to longitudinal axis A is for purposes of illustration and should not be considered limiting. According to various embodiments, the packing angle of surgical clips 1510a-f with respect to longitudinal axis A may be non-zero and range between about 1 degree and about 89 degrees. In more specific embodiments, the packing angle may range between about 10 degrees and about 60 degrees, or between about 15 degrees and about 50 degrees, or between about 20 degrees and about 45 degrees, or between about 25 degrees and about 40 degrees, or between about 20 degrees and 50 degrees, or between about 20 degrees and about 40 degrees, or between about 20 degrees and about 30 degrees, or between about 5 degrees and about 20 degrees, or between about 5 degrees and about 15 degrees, or between about 10 degrees and about 20 degrees, or between about 10 degrees and about 15 degrees. Surgical clip 1510a need not necessarily be seated at the same angle as surgical clips 1510b-f, as discussed further below. The non-zero packing angle may be chosen to constrain surgical clips 1510a-f within a given longitudinal length (space) and to define a radial profile below a desired height (e.g., below the crown-to-tail height of surgical clips 1510a-f stacked perpendicular to longitudinal axis A).

Furthermore, according to some embodiments, surgical clips 1510a-f or another suitable number of surgical clips may be added to end effector 1500 in a cartridge, magazine, or similar structure.

As depicted, surgical clip feeders 1502a and 1502b include surgical clips 1510a-f arranged with the crowns of the more distal surgical clips overlapping the tail (i.e., the legs) of the more proximal surgical clips. As depicted in FIG. 17, for example, the crown of distal-most surgical clip 1510a overlays at least a portion of the tail of penultimate (next-most distal) surgical clip 1510b, with remaining surgical clips 1510c-f overlapping or nesting in a similar manner. The extent and angle of overlayment between surgical clips 1510a-f may be the same or different depending on their longitudinal positioning. The positioning and angle of distal-most surgical clips 1510a, for example, may be influenced by the inner surface (contour or internally tapered surface) of tapered section 1602 (FIG. 16) and different than that of surgical clips 1510b-f. Distal-most surgical clips 1510a are engaged internally with tapered section 1602, as described hereinafter.

Surgical clip feeders 1502a and 1502b are configured for selectively advancing surgical clips 1510a-f distally. As depicted in FIGS. 17 and 18, for example, surgical clip feeders 1502a and 1502b are distally biased with corresponding feed springs 1512a and 1512b, which are engaged with clip shoes 1514a and 1514b, respectively. Clip shoes 1514a and 1514b are configured to transfer a longitudinal (axial) load from feed springs 1512a and 1512b to surgical clips 1510a-f in surgical clip feeder 1502a and 1502b, respectively, in order to promote distal translation thereof. As with end effector 1100, alternative mechanisms, such as those incorporating electrical, mechanical, electromechanical, hydraulic, pneumatic, or magnetic biasing principles, for example, may be used in place of feed springs 1512a and/or 1512b. Moreover, other techniques for applying a longitudinal (axial) load to clip shoes 1514a and 1514b also reside within the scope of the present disclosure. In some embodiments, for example, compression spring(s) 1512a and/or 1512b may be replaced with a push rod or like structure that may be selectively actuated directly from a drive housing or via a geared assembly or the like. In embodiments with a geared assembly, for example, the push rod may be operatively coupled to a cable-driven worm gear positioned adjacent surgical clip feeder 1502a and/or 1502b and associated drive cable(s) that move the worm gear may extend thereto from a drive housing and potentially through a wrist.

As shown in FIG. 18, end effector 1500 further includes upper feedbar 1530a and lower feedbar 1530b. Upper and lower feedbars 1530a and 1530b may be configured for longitudinal movement between surgical clips 1510b-f and the inner surface of housing 1600 proximal to tapered section 1602 (FIG. 16) and its internally tapered surface. In operation, upper and lower feedbars 1530a and 1530b selectively advance distal-most surgical clip 1510a from adjacent to tapered section 1602 (FIG. 16) into clip track 1780 and between jaw members 1511a and 1511b. To accomplish this feature, upper and lower feedbars 1530a and 1530b may be capable of following the contour (internally tapered surface) of tapered section 1602, as discussed below.

To facilitate movement along tapered section 1602, upper and lower feedbars 1530a and 1530b may include distal portions 1702a and 1702b, respectively, that are configured to follow the contour of inner wall 1705 (FIG. 19) of tapered section 1602. Distal portions 1702a and 1702b each comprise distal end 1800 that is configured to engage the crown of a surgical clip within tapered section 1602, thereby promoting distal advancement thereof.

According to some embodiments, and as depicted in FIG. 18, distal ends 1800 may provide a complementary profile configured to mate with the crown of the surgical clips (i.e., surgical clip 1510a in the depicted configuration). Proximal to tapered section 1602 (FIG. 16), in contrast, distal ends 1800 are unable to advance surgical clips 1510b-f by similarly engaging their crowns. However, upon distal advancement of surgical clips 1510b-f into an internal position adjacent to tapered section 1602, upper and lower feedbars 1530a and 1530b may also promote further distal advancement of surgical clips 1510b-f. Upper and lower feedbars 1530a and 1530b may be independently actuated via an input from a drive housing (not shown) and associated components thereof, as generally discussed above, to selectively advance surgical clips 1510a-f individually into interposition between jaw members 1511a and 1511b. In at least one embodiment, surgical clips 1510a-f may reside in a groove (not shown) when positioned between jaw members 1511a and 1511b.

In some embodiments, and as depicted, upper and lower feedbars 1530a and 1530b may each include hinge 1700, which is configured to allow distal portions 1702a and 1702b of upper and lower feedbars 1530a and 1530b, respectively, to follow the contour (internally tapered surface) of inner wall 1705 (FIG. 19) of tapered section 1602 (FIG. 16). More specifically, hinge 1700 allows distal portions 1702a and 1702b to engage the inner surface of housing 1600 (FIG. 16) within tapered section 1602 and flex inward toward longitudinal axis A. In at least one embodiment, hinge 1700 may constitute a living hinge, but may alternatively be any other type of hinged configuration that allows distal portions 1702a and 1702b to flex inward in a similar manner. Non-hinged alternative configurations of upper and lower feedbars 1530a and 1530b that are similarly capable of flexing inward toward longitudinal axis A and translating along tapered section 1602 also reside within the scope of the present disclosure. In at least one embodiment, for example, at least one of upper and lower feedbars 1530a and 1530b may be a segmented or non-segmented rod that is capable of traversing along inner wall 1705 (FIG. 19) of tapered section 1602. In some or other embodiments, upper and lower feedbars 1530a and 1530b may comprise a flexible material that is able to elastically bend as it follows the contour (internally tapered surface) of tapered section 1602. According to some embodiments, the flexible material may be located in a flexible segment interposed between two rigid segments of upper and/or lower feedbars 1530a and 1530b, which allows the flexure location to change during distal advancement and withdrawal.

Once distal-most surgical clip 1510a has been properly positioned between jaw members 1511a and 1511b, camming mechanism 1740 (one visible in FIG. 18) may be actuated and translated distally to engage cam tracks 1770 and thereby urge jaw members 1511*a* and 1511*b* toward one another to crimp surgical clip 1510*a* positioned therebetween. Camming mechanism 1740 is interposed between surgical clips 1510*a-f* within surgical clip feeders 1502*a* and 1502*b*. As depicted, cam tracks 1770 comprise opposing lobes defined on an outer surface of jaw members 1511*a* and 1511*b*, but may alternatively comprise other types of camming configurations known in the art without departing from the scope of the present disclosure. Alternative mechanisms for urging jaw members 1511*a* and 1511*b* toward one another also reside within the scope of the present disclosure.

Jaw members 1511*a* and 1511*b* may be naturally biased to an open position to receive surgical clip 1510*a* and subsequent surgical clips. Consequently, distal withdrawal of camming mechanism 1540 allows jaw members 1511*a* and 1511*b* to return to the open position or otherwise move away from one another to release surgical clip 1210*a* in a crimped state.

Figure 19:
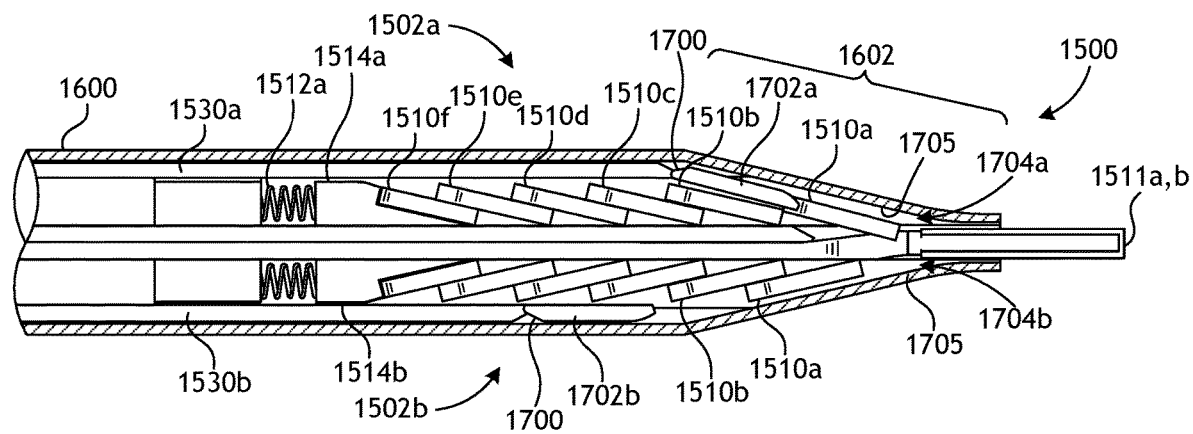
FIGS. 19 and 20 are corresponding cross-sectional views of the second end effector at various operational stages.
Figure 20:
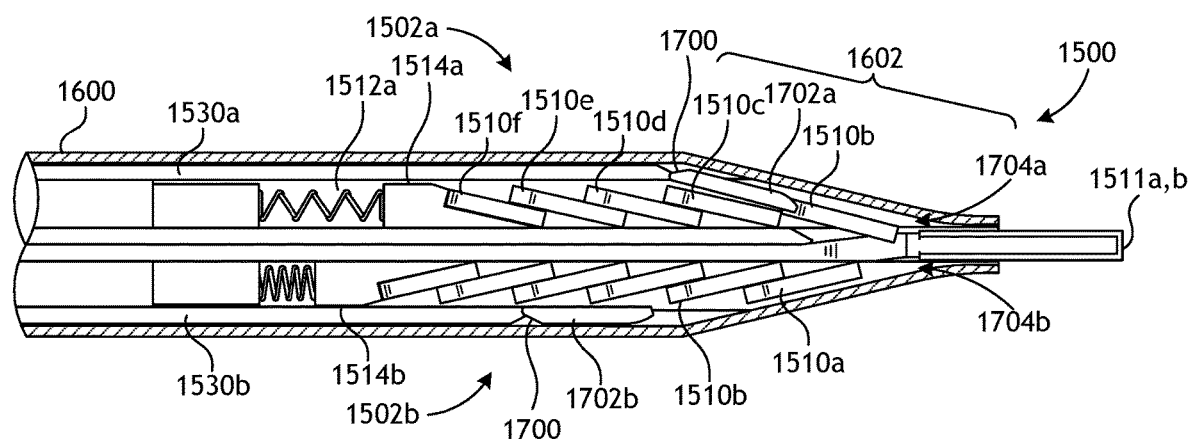

FIGS. 19 and 20 are cross-sectional views of end effector 1500 at various operational stages thereof, in which additional details concerning distal advancement of surgical clips 1510*a-f* are provided. As shown in FIG. 19, surgical clips 1510*a-f* are advanced distally via the longitudinal biasing force supplied by feed spring 1512*a* and clip shoe 1514*a* until each surgical clip 1510*a* engages inner wall 1705 of tapered section 1602 within channel 1704*a* and does not advance further distally. At this location and as discussed in detail above, distal portion 1702*a* of upper feedbar 1530*a* may then engage surgical clip 1510*a* to distally advance surgical clip 1510*a* further through channel 1704*a* and into clip track 1780 (FIG. 18). Hinge 1700 allows upper feedbar 1530*a* to follow the contour of tapered section 1602 and engage surgical clip 1510*a* within channel 1704*a*. Continued distal advancement of surgical clip 1510*a* with upper feedbar 1530*a* results in interpositioning of surgical clip 1510*a* between jaw members 1511*a* and 1511*b*. Distal portion 1702*a* may be of sufficient length to translate surgical clip 1510*a* through channel 1704*a* and clip track 1780 to a position between jaw members 1511*a* and 1511*b*.

Once surgical clip 1510*a* has advanced through channel 1704*a*, distal portion 1702*a* of upper feedbar 1530*a* occludes further distal advancement of penultimate surgical clip 1510*b* into channel 1704*a*. Following sufficient proximal withdrawal of upper feedbar 1530*a*, distal portion 1702*a* exits channel 1704*a* and clears the way for distal advancement of remaining surgical clips 1510*b-f* via feed spring 1512*a* and clip shoe 1514*a* until surgical clip 1510*b* becomes engaged with inner wall 1705 (internally tapered surface) of tapered section 1602, as shown in FIG. 20. Inner wall 1705 may then guide surgical clip 1510*b* as it is deployed into interposition between jaw members 1511*a* and 1511*b* in a similar manner to that discussed above for surgical clip 1510*a*.

Distal portion 1702*b* of lower feedbar 1530*b* may similarly traverse channel 1704*b* to promote independent distal translation of surgical clip 1510*a* therethrough. The remaining surgical clips in surgical clip feeder 1502*b* may likewise be deployed in a manner similar to that described above for surgical clip feeder 1502*a*. Although FIGS. 19 and 20 have depicted distal portions 1702*a* and 1702*b* as having a similar size, it is appreciated that these elements may differ in size, according to one or more embodiments. For example, if surgical clip feeders 1502*a* and 1502*b* contain surgical clips 1510*a-f* of differing sizes (e.g., crown-to-tail distance, leg opening, or the like), distal portions 1702*a* and 1702*b* may be sized differently to facilitate proper clip movement through channels 1704*a* and 1704*b*.

In some embodiments, operation (dispensation) of surgical clip feeder 1502*b* may alternate with operation (dispensation) of surgical clip feeder 1502*a* (i.e., the operation order may be surgical clips 1510*a*, 1510*a*, 1510*b*, 1510*b*, 1510*c*, 1510*c*, 1510*d*, 1510*d*, 1510*e*, 1510*e*, 1510*f*, 1510*f*), wherein either surgical clip feeder 1502*a* or 1502*b* may be operated first. In other embodiments, surgical clip feeders 1502*a* and 1502*b* may be operated sequentially (i.e., the operation order is surgical clips 1510*a*, 1510*b*, 1510*c*, 1510*d*, 1510*e*, 1510*f*, 1510*a*, 1510*b*, 1510*c*, 1510*d*, 1510*e*, 1510*f*), again with either surgical clip feeder 1502*a* or 1502*b* being operated first until its supply of surgical clips is exhausted. Combinations of these approaches may be employed as well.

The order of clip dispensation from surgical clip feeders 1502*a* and 1502*b* may alternatively be influenced by other various factors. For example, in some embodiments, the surgical clips housed in surgical clip feeder 1502*a* may be a different size, type or shape than the surgical clips housed in surgical clip feeder 1502*b*. As such, a medical practitioner may selectively dispense surgical clip feeders 1502*a* and 1502*b* in any order required to perform a given surgical procedure.

Clip dispensation from surgical clip feeders 1502*a* and 1502*b* may be monitored by various software controls and inform the medical practitioner of the number of surgical clips remaining in each of surgical clip feeders 1502*a* and 1502*b*. In some embodiments, the software controls can further inform the medical practitioner of the size and/or type of the surgical clips present and the number of surgical clips of each size and/or type remaining in surgical clip feeders 1502*a* and 1502*b*. Differently colored surgical clips, for example, may be housed in surgical clip feeders 1502*a* and 1502*b*, wherein the differently colored surgical clips may be employed for internal marking during a surgical procedure. The software controls may further provide an alarm or reminder that a surgical clip of a given size or type is about to be fired from surgical tool 1500, which may provide a failsafe against unwanted deployment of a surgical clip of improper size or type.

It is to be further appreciated that while FIGS. 17-20 have depicted surgical clip feeders 1502*a* and 1502*b* as containing six surgical clips 1110*a-f* in an angled longitudinal packing arrangement, this number is exemplary for purposes of illustration. In illustrative embodiments, surgical clip feeders 1502*a* and 1502*b* may contain two or more surgical clips in an angled longitudinal packing orientation. The number of surgical clips within surgical clip feeders 1502*a* and 1502*b* may be the same or different. In various embodiments, surgical clip feeders 1502*a* and 1502*b* may contain between five and ten surgical clips, or between two and six surgical clips, or between two and four surgical clips, or two surgical clips, or three surgical clips, or four surgical clips, or five surgical clips, or six surgical clips. Again, the number of surgical clips that may be accommodated within surgical clip feeders 1502*a* and 1502*b* may be dictated by various factors, such as the amount of longitudinal space available in a given surgical tool distal to the wrist and the crown-to-tail distance of the surgical clips employed. In cases of non-wristed clip appliers, at least a portion of the elongate shaft may be utilized to house surgical clips, and many more surgical clips may be accommodated, such as between about 20 and about 40 surgical clips, limited only by the elongate shaft length.

Figure 21:
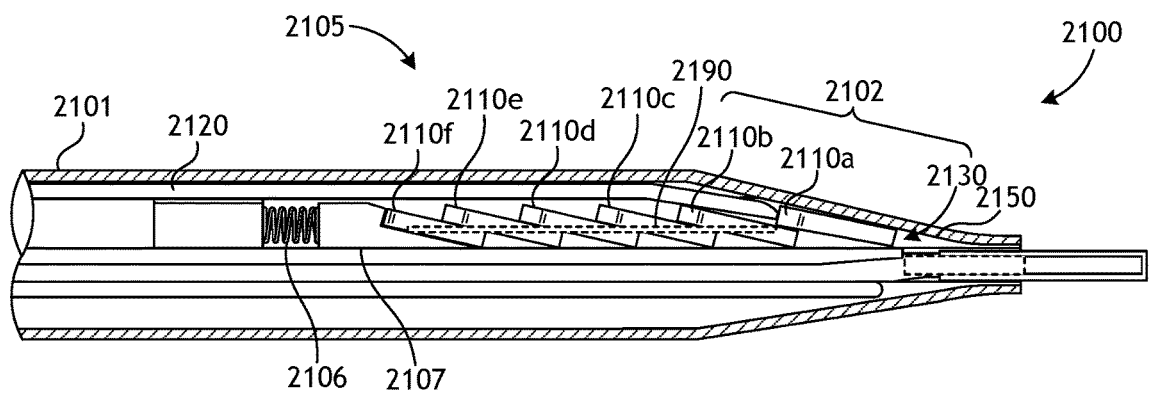
FIGS. 21-23 are cross-sectional views of a third end effector of the present disclosure at various operational stages.
Figure 22:
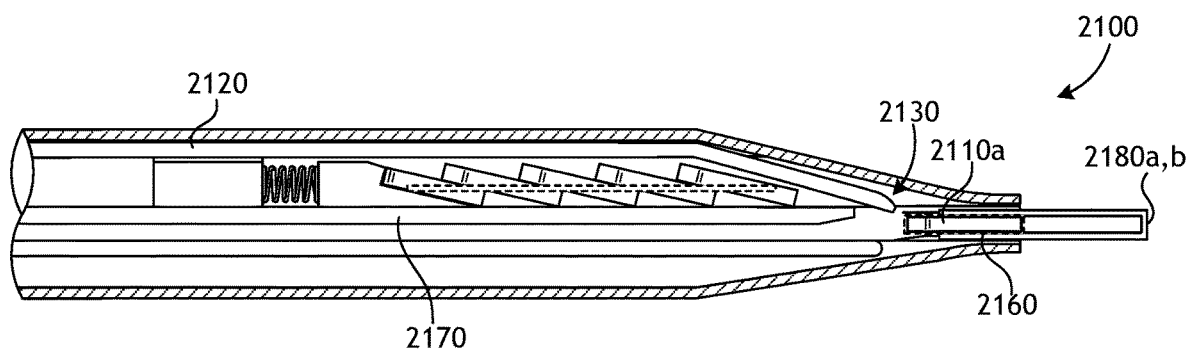
Figure 23:
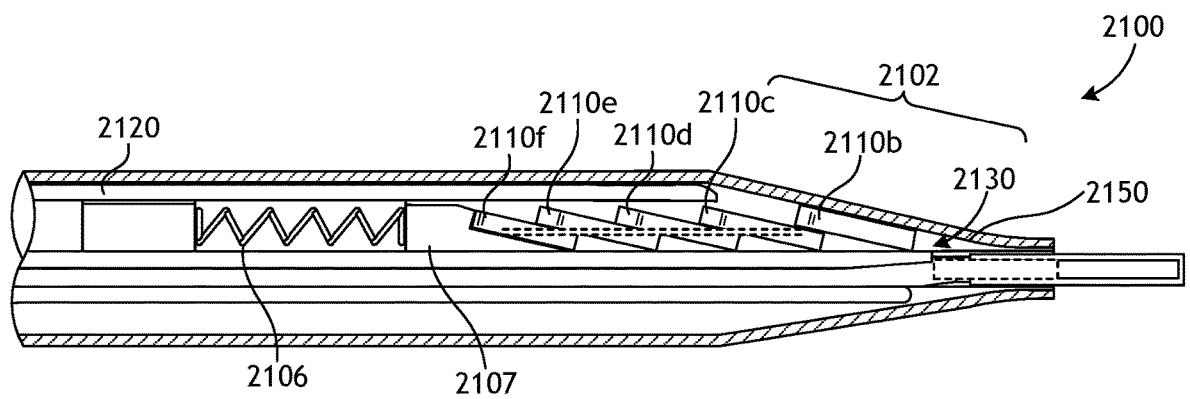

In still other various embodiments, assorted features of end effectors 1100 and 1500 may be combined in an end effector employing operational principles of each, as shown in the cross-sectional views of FIGS. 21-23. In particular, end effector 2100 combines the concepts of angled surgical clip packing and a flexible "upper" feedbar, similar to the description above for end effector 1500, and a rigid or semi-rigid "lower" feedbar, similar to that described above for end effector 1100. The "dual" feedbars of end effector 2100 may facilitate surgical clip translation at different locations, as described in further detail hereinafter.

Referring to FIG. 21, end effector 2100 includes housing 2101, which includes tapered section 2102 at its distal end. Surgical clips 2110a-f are arranged in an angled packing orientation within housing 2101, such that the crowns of the more distal surgical clips overlap the tails (i.e., the legs) of the more proximal surgical clips. According to some embodiments, at least a portion of surgical clips 2110a-f in end effector 2100 may be arranged around central support 2190 to aid in maintaining proper clip positioning. Central support 2190 may be fixed or telescoping, according to various embodiments. It is to be further appreciated that end effector 2100 may be operatively coupled to a wrist similar to wrist 606 (FIG. 6), as well as other previously described features and components suitable for articulating, rotating and/or actuating the components comprising end effector 2100. As such, for example, it is to be appreciated that drive inputs and capstans similar to drive inputs 906a-f (FIG. 9) and capstans 1002a-f (FIG. 10) and their associated features may be in communication with one or more of the various components depicted in FIGS. 21-23 in order to affect operation thereof. Moreover, it is to be further appreciated that end effector 2100 may be employed in non-wristed surgical tools as well.

End effector 2100 includes surgical clip feeder 2105 that is configured for advancing surgical clips 2110a-f distally. Surgical clip feeder 2105 includes feed spring 2106 and clip shoe 2107, which are configured to deliver a longitudinal biasing load onto surgical clips 2110a-f. As with end effectors 1100 and 1500, alternative mechanisms, such as those incorporating electrical, mechanical, electromechanical, hydraulic, pneumatic, or magnetic biasing principles, for example, may be used in place of feed spring 2106. Moreover, other techniques for applying a longitudinal load also reside within the scope of the present disclosure, such concepts employing a push rod or like structure that may be selectively actuated directly from a drive housing or via a geared assembly or the like.

The longitudinal biasing force applied by feed spring 2106 and clip shoe 2107 urges surgical clips 2110a-f distally until distal-most surgical clip 2110a becomes engaged with inner wall 2150 of tapered section 2102. Inner wall 2150 defines an internally tapered surface within tapered section 2102. Upper feedbar 2120 may then be actuated to engage surgical clip 2110a within channel 2130, which is defined, in part, by inner wall 2150 of tapered section 2102. As with end effector 1500, upper feedbar 2120 is sufficiently flexible to extend into channel 2130 for engaging the crown of surgical clip 2110a therein. Upper feedbar 2120 may be hinged or non-hinged, according to various embodiments.

As shown in FIG. 22, upper feedbar 2120 may advance surgical clip 2110a distally into clip track 2160. Clip track 2160 provides an intermediate feeding location for surgical clip 2110a. Once surgical clip 2110a has been positioned in clip track 2160, as shown in FIG. 22, lower feedbar 2170 may then be advanced distally to engage the crown of surgical clip 2110a to complete advancement thereof into interposition between jaw members 2180a and 2180b. Lower feedbar 2170 may be adapted to translate longitudinally within clip track 2160 based upon an input from a corresponding drive housing (not shown). According to various embodiments, lower feedbar 2170 or a component thereof may extend through a wrist (not shown) in order to aid in positioning surgical clip 2110a between jaw members 2180a and 2180b during use. Once surgical clip 2110a has been suitably positioned between jaw members 2180a and 2180b, cam-induced closure of jaw members 2180a and 2180b, or another suitable closure process, may take place to promote crimping.

Jaw members 2180a and 2180b may be naturally biased to an open position to receive surgical clip 2110a and subsequent surgical clips. Consequently, jaw members 2180a and 2180b may return to the open position or otherwise move away from one another once no longer subjected to a camming force.

While positioned in channel 2130, either before or after advancing surgical clip 2110a, upper feedbar 2120 occludes channel 2130 and precludes further distal advancement of surgical clips 2110b-f. Following proximal retraction of upper feedbar 2120 out of channel 2130, however, the longitudinal biasing force supplied by feed spring 2106 and clip shoe 2107 may urge surgical clips 2110b-f distally, as shown in FIG. 23. In particular, the longitudinal biasing force urges surgical clips 2110b-f distally until surgical clip 2110b enters channel 2130 and becomes engaged with inner wall 2150 of tapered section 2102. At this point, surgical clip 2110b may be further manipulated as described above for surgical clip 2110a.

Embodiments disclosed herein include:

A. End effectors for surgical clip applier. The end effectors comprise: a housing having a tapered section at a distal end thereof; first and second jaw members protruding distally from the tapered section; a surgical clip feeder arranged within the housing and configured to contain a plurality of surgical clips therein; wherein the plurality of surgical clips are arrangeable within the surgical clip feeder at a non-zero angle with respect to a longitudinal axis of the end effector; and a feedbar longitudinally movable between the housing and the plurality of surgical clips, the feedbar having a distal portion engageable with a distal-most surgical clip of the plurality of surgical clips within the tapered section; wherein actuation of the feedbar engages and advances the distal-most surgical clip out of the surgical clip feeder and into interposition between the first and second jaw members.

B. Surgical tools. The surgical tools comprise: a drive housing; an elongate shaft extending from the drive housing; and an end effector operatively coupled to a distal end of the elongate shaft, the end effector comprising: a housing having a tapered section at a distal end thereof; first and second jaw members protruding distally from the tapered section; a surgical clip feeder arranged within the housing and configured to contain a plurality of surgical clips therein; wherein the plurality of surgical clips are arrangeable within the surgical clip feeder at a non-zero angle with respect to a longitudinal axis of the end effector; and a feedbar longitudinally movable between the housing and the plurality of surgical clips, the feedbar having a distal portion engageable with a distal-most surgical clip of the plurality of surgical clips within the tapered section; wherein actuation of the feedbar engages and advances the distal-most surgical clip out of the surgical clip feeder and into interposition between the first and second jaw members.

C. Methods for using a surgical tool. The methods comprise: positioning a surgical tool having an end effector adjacent to a surgical site, the end effector comprising: a housing having a tapered section at a distal end thereof; first and second jaw members protruding distally from the tapered section; a surgical clip feeder arranged within the housing and containing a plurality of surgical clips therein, the plurality of surgical clips including a distal-most surgical clip and a penultimate surgical clip; wherein the plurality of surgical clips are arranged within the surgical clip feeder at a non-zero angle with respect to a longitudinal axis of the end effector; and a feedbar longitudinally movable between the housing and the plurality of surgical clips, the feedbar having a distal portion engageable with the distal-most surgical clip; advancing the feedbar distally to engage the distal-most surgical clip, the distal-most surgical clip being in engagement with an inner wall of the tapered section; distally advancing the distal-most surgical clip out of the surgical clip feeder with the feedbar and into interposition between the first and second jaw members; wherein the inner wall of the tapered section redirects the distal-most surgical clip as the distal-most surgical clip advances distally; and at least partially collapsing the first and second jaw members to crimp the distal-most surgical clip once positioned therebetween.

Each of embodiments A, B, and C may have one or more of the following additional elements in any combination Element 1: wherein the feedbar includes a hinge and the distal portion is located distal to the hinge to allow the feedbar to follow a contour of the tapered section.

Element 2: wherein the feedbar comprises a flexible material that allows the feedbar to follow a contour of the tapered section.

Element 3: wherein the surgical clip feeder comprises a distally biased clip shoe.

Element 4: wherein the end effector further comprises a camming mechanism configured to actuate the first and second jaw members.

Element 5: wherein a crown of a more distal surgical clip within of the plurality of surgical clips at least partially overlays a tail of a more proximal surgical clip within of the plurality of surgical clips.

Element 6: wherein the surgical clip feeder is a first surgical clip feeder positioned in a first hemisphere of the housing, the plurality of surgical clips is a first plurality of surgical clips, and the feedbar is a first feedbar, the end effector further comprising: a second surgical clip feeder positioned in a second hemisphere of the housing opposite the first hemisphere and configured to contain a second plurality of surgical clips therein; wherein the second plurality of surgical clips are arrangeable within the second surgical clip feeder at a non-zero angle with respect to the longitudinal axis of the end effector; and a second feedbar longitudinally movable between the housing and the second plurality of surgical clips, the second feedbar having a distal portion engageable with a distal-most surgical clip of the second plurality of surgical clips within the tapered section; wherein actuation of the second feedbar engages and advances the distal-most surgical clip out of the second surgical clip feeder and into interposition between the first and second jaw members.

Element 7: wherein at least one of the first feedbar and the second feedbar includes a hinge and the distal portion is located distal to the hinge to allow the at least one of the first feedbar and the second feedbar to follow a contour of the tapered section.

Element 8: wherein at least one of the first feedbar and the second feedbar comprises a flexible material that allows the at least one of the first feedbar and the second feedbar to follow a contour of the tapered section.

Element 9: wherein the first and second feedbars are independently actuatable.

Element 10: wherein the first and second surgical clip feeders each comprise a distally biased clip shoe.

Element 11: wherein the end effector further comprises a camming mechanism configured to actuate the first and second jaw members, the camming mechanism being interposed between the first and second surgical clip feeders.

Element 12: wherein the first plurality of surgical clips and the second plurality of surgical clips differ in at least one of size and type.

Element 13: wherein the surgical tool further comprises a wrist coupling the distal end of the elongate shaft to the end effector.

Element 14: wherein the method further comprises proximally withdrawing the feedbar from the tapered section; and after withdrawing the feedbar from the tapered section, actuating the surgical clip feeder to advance the penultimate surgical clip distally into the tapered section.

Element 15: wherein the surgical clip feeder is distally biased and autonomously advances the penultimate surgical clip into engagement with the inner wall of the tapered section.

By way of non-limiting example, exemplary combinations applicable to A, B, and C include: The end effector of A in combination with elements 1 or 2, and 3; 1 or 2, and 4; 1 or 2, and 5; 3 and 4; 3 and 5; 4 and 5; 6, and 7 or 8; 6 and 9; 6, 7 or 8, and 9; 6 and 10; 6 and 11; 6, 7 or 8, and 11; 6, 7 or 8, 9, and 10; 6, 7 or 8, 9 and 11; and 6 and 12. The surgical tool of B in combination with elements 1 or 2, and 3; 1 or 2, and 4; 1 or 2, and 5; 3 and 4; 3 and 5; 4 and 5; 6, and 7 or 8; 6 and 9; 6, 7 or 8, and 9; 6 and 10; 6 and 11; 6, 7 or 8, and 11; 6, 7 or 8, 9, and 10; 6, 7 or 8, 9 and 11; and 6 and 12, any of which may be in further combination with element 13. The method of C in combination with elements 1 or 2, and 3; 1 or 2, and 4; 1 or 2, and 5; 3 and 4; 3 and 5; 4 and 5; 6, and 7 or 8; 6 and 9; 6, 7 or 8, and 9; 6 and 10; 6 and 11; 6, 7 or 8, and 11; 6, 7 or 8, 9, and 10; 6, 7 or 8, 9 and 11; 6 and 12; and 14 and 15, any of which may be in further combination with element 13.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An end effector for a surgical clip applier, comprising:
   a housing having a tapered section at a distal end;
   first and second jaw members protruding distally from the tapered section;
   a surgical clip feeder arranged within the housing and containing a plurality of surgical clips arranged at a non-zero angle with respect to a longitudinal axis of the end effector, wherein a distal-most surgical clip of the plurality of surgical clips is engageable with an inner wall of the tapered section; and
   a feedbar longitudinally movable between the housing and the plurality of surgical clips, the feedbar having a distal portion engageable with the inner wall and the distal-most surgical clip and being flexible to follow a contour of the tapered section,
   wherein actuation of the feedbar engages and advances the distal-most surgical clip out of the surgical clip feeder and into interposition between the first and second jaw members.

2. The end effector of claim 1, wherein the feedbar includes a hinge and the distal portion is located distal to the hinge to allow the feedbar to follow the contour of the tapered section.

3. The end effector of claim 1, wherein the feedbar is made of a flexible material that allows the feedbar to follow the contour of the tapered section.

4. The end effector of claim 1, wherein the surgical clip feeder comprises a distally biased clip shoe.

5. The end effector of claim 1, further comprising a camming mechanism configured to actuate the first and second jaw members.

6. The end effector of claim 1, wherein a crown of a more distal surgical clip within of the plurality of surgical clips at least partially overlays a tail of a more proximal surgical clip within the plurality of surgical clips.

7. The end effector of claim 1, wherein the surgical clip feeder is a first surgical clip feeder positioned in a first hemisphere of the housing, the plurality of surgical clips is a first plurality of surgical clips, and the feedbar is a first feedbar, the end effector further comprising:
   a second surgical clip feeder positioned in a second hemisphere of the housing opposite the first hemisphere and containing a second plurality of surgical clips arranged at a non-zero angle with respect to the longitudinal axis of the end effector, wherein a distal-most surgical clip of the second plurality of surgical clips is engageable with the inner wall of the tapered section; and
   a second feedbar longitudinally movable between the housing and the second plurality of surgical clips, the second feedbar having a distal portion engageable with the inner wall and the distal-most surgical clip of the second plurality of surgical clips and being flexible to follow the contour of the tapered section,
   wherein actuation of the second feedbar engages and advances the distal-most surgical clip out of the second surgical clip feeder and into interposition between the first and second jaw members.

8. The end effector of claim 7, wherein at least one of the first feedbar and the second feedbar includes a hinge and the distal portion is located distal to the hinge to allow the at least one of the first feedbar and the second feedbar to follow the contour of the tapered section.

9. The end effector of claim 7, wherein at least one of the first feedbar and the second feedbar is made of a flexible material that allows the at least one of the first feedbar and the second feedbar to follow the contour of the tapered section.

10. The end effector of claim 7, wherein the first and second feedbars are independently actuatable.

11. The end effector of claim 7, wherein the first and second surgical clip feeders each comprise a distally biased clip shoe.

12. The end effector of claim 7, further comprising a camming mechanism configured to actuate the first and second jaw members, the camming mechanism being interposed between the first and second surgical clip feeders.

13. The end effector of claim 7, wherein the first plurality of surgical clips and the second plurality of surgical clips differ in at least one of size and type.

14. A surgical tool comprising:
    a drive housing;
    an elongate shaft extending from the drive housing; and
    an end effector operatively coupled to a distal end of the elongate shaft and comprising:
      a housing having a tapered section at a distal end;
      first and second jaw members protruding distally from the tapered section;
      a surgical clip feeder arranged within the housing and containing a plurality of surgical clips arranged at a non-zero angle with respect to a longitudinal axis of the end effector, wherein a distal-most surgical clip of the plurality of surgical clips is engageable with an inner wall of the tapered section; and
    a feedbar longitudinally movable between the housing and the plurality of surgical clips, the feedbar having a distal portion engageable with the inner wall and the distal-most surgical clip and being flexible to follow a contour of the tapered section,
    wherein actuation of the feedbar engages and advances the distal-most surgical clip out of the surgical clip feeder and into interposition between the first and second jaw members.

15. The surgical tool of claim 14, further comprising a wrist coupling the distal end of the elongate shaft to the end effector.

16. The surgical tool of claim 14, wherein the surgical clip feeder is a first surgical clip feeder positioned in a first hemisphere of the housing, the plurality of surgical clips is a first plurality of surgical clips, and the feedbar is a first feedbar, the end effector further comprising:
- a second surgical clip feeder positioned in a second hemisphere of the housing opposite the first hemisphere and containing a second plurality of surgical clips arranged at a non-zero angle with respect to the longitudinal axis of the end effector, wherein a distal-most surgical clip of the second plurality of surgical clips is engageable with the inner wall of the tapered section; and
- a second feedbar longitudinally movable between the housing and the second plurality of surgical clips, the second feedbar having a distal portion engageable with the inner wall and the distal-most surgical clip of the second plurality of surgical clips and being flexible to follow a contour of the tapered section,
- wherein actuation of the second feedbar engages and advances the distal-most surgical clip out of the second surgical clip feeder and into interposition between the first and second jaw members.

17. The surgical tool of claim 14, wherein at least one of the first feedbar and the second feedbar includes a hinge and the distal portion is located distal to the hinge to allow the at least one of the first feedbar and the second feedbar to follow the contour of the tapered section.

18. A method comprising:
   positioning a surgical tool having an end effector adjacent to a surgical site, the end effector comprising:
   - a housing having a tapered section at a distal end thereof;
   - first and second jaw members protruding distally from the tapered section;
   - a surgical clip feeder arranged within the housing and containing a plurality of surgical clips therein, the plurality of surgical clips including a distal-most surgical clip and a penultimate surgical clip;
   - wherein the plurality of surgical clips are arranged within the surgical clip feeder at a non-zero angle with respect to a longitudinal axis of the end effector; and
   - a feedbar longitudinally movable between the housing and the plurality of surgical clips, the feedbar having a distal portion engageable with the distal-most surgical clip;
   advancing the feedbar distally to engage an inner wall of the tapered section and the distal-most surgical clip, the distal-most surgical clip being in engagement with the inner wall and the feedbar being flexible to follow a contour of the tapered section;
   distally advancing the distal-most surgical clip out of the surgical clip feeder with the feedbar and into interposition between the first and second jaw members wherein the inner wall of the tapered section redirects the distal-most surgical clip and the feedbar as the distal-most surgical clip advances distally; and
   at least partially collapsing the first and second jaw members to crimp the distal-most surgical clip once positioned therebetween.

19. The method of claim 18, further comprising:
   proximally withdrawing the feedbar from the tapered section; and
   after withdrawing the feedbar from the tapered section, actuating the surgical clip feeder to advance the penultimate surgical clip distally into the tapered section.

20. The method of claim 19, wherein the surgical clip feeder is distally biased and autonomously advances the penultimate surgical clip into engagement with the inner wall of the tapered section.

\* \* \* \* \*